United States Patent
Hermida Cruz et al.

(10) Patent No.: US 9,463,235 B2
(45) Date of Patent: Oct. 11, 2016

(54) DENGUE VIRUS VACCINE COMPOSITION

(71) Applicant: Centro de Ingeniería Genética y Biotecnología, La Habana (CU)

(72) Inventors: Lisset Hermida Cruz, La Habana (CU); Lázaro Gil González, Mayabeque (CU); Alienys Izquierdo Oliva, Artemisa (CU); Ernesto Marcos López, La Habana (CU); Edith Suzarte Portal, La Habana (CU); Gerardo Enrique Guillén Nieto, La Habana (CU); María Guadalupe Guzmán Tirado, La Habana (CU); Iris Valdés Prado, La Habana (CU); Laura Lazo Vazquez, La Habana (CU); Angelica de la Caridad Garcia Arechavaleta, La Habana (CU); Mayling Alvarez Vera, La Habana (CU); Jorge Castro Velazco, La Habana (CU); Lázaro López Fernández, Artemisa (CU); Rosa Liset Ramírez Bartutis, La Habana (CU); Yusleidi de la Caridad Pérez Fuentes, La Habana (CU); Olga Lidia Pérez Guevara, La Habana (CU); Yaremy Romero Fernández, La Habana (CU)

(73) Assignee: CENTRO DE INGENIERÍA GENEÉTICA Y BIOTECHNOLOGÍA, La Habana (CU)

( * ) Notice: Subject to any disclaimer, the term of this patent is extended or adjusted under 35 U.S.C. 154(b) by 0 days.

(21) Appl. No.: 14/655,227

(22) PCT Filed: Dec. 16, 2013

(86) PCT No.: PCT/CU2013/000008
§ 371 (c)(1),
(2) Date: Jun. 24, 2015

(87) PCT Pub. No.: WO2014/101903
PCT Pub. Date: Jul. 3, 2014

(65) Prior Publication Data
US 2015/0328304 A1 Nov. 19, 2015

(30) Foreign Application Priority Data

Dec. 27, 2012 (CU) .................................. 2012-0179

(51) Int. Cl.
*A61K 39/12* (2006.01)
*C07K 14/005* (2006.01)
(Continued)

(52) U.S. Cl.
CPC ........... *A61K 39/12* (2013.01); *A61K 2039/53* (2013.01); *A61K 2039/55505* (2013.01);
(Continued)

(58) Field of Classification Search
CPC .......... C12N 7/00; C12N 2770/24134; C12N 2770/24122; C12N 2770/36134; C12N 2770/24121; C12N 2770/24151; C12N 2770/24161; C12N 2770/00; C12N 2770/24123; C12N 2770/24133; C12N 7/02; C07K 14/005
See application file for complete search history.

(56) References Cited

U.S. PATENT DOCUMENTS 6,383,488 B1 * 5/2002 Ramudo .............. C07K 14/005 424/130.1
7,279,164 B2 * 10/2007 Hermida Cruz ..... C07K 14/005 424/185.1

(Continued)

FOREIGN PATENT DOCUMENTS

WO WO2007031034 A1 3/2007

OTHER PUBLICATIONS

Clements DE, Coller BA, Lieberman MM, Ogata S, Wang G, Harada KE, Putnak JR, Ivy JM, McDonell M, Bignami GS, Peters ID, Leung J, Weeks-Levy C, Nakano ET, Humphreys T. Development of a recombinant tetravalent dengue virus vaccine: immunogenicity and efficacy studies in mice and monkeys. Vaccine. Mar. 24, 2010;28(15):2705-15. Epub Jan. 22, 2010.*

(Continued)

*Primary Examiner* — Rachel B Gill
(74) *Attorney, Agent, or Firm* — Hoffmann & Baron, LLP

(57) ABSTRACT

Vaccine compositions that comprise at least one antigen based on the dengue virus (DV) capsid protein and the oligonucleotide identified as SEQ ID NO 1. The vaccine composition that comprises a fusion protein formed by the DV2 capsid and domain III of the envelope protein of the same serotype, together with the oligonucleotide identified as SEQ ID NO 1, gives rise to higher levels of cellular immune response and protection in mice as compared with that produced by formulations of the same antigen together with oligonucleotides with potential adjuvant capacity which were reported previously. The efficacy of the compositions that comprise the SEQ ID NO 1 oligonucleotide has been demonstrated in non-human primates. These compositions may be monovalent, bivalent or tetravalent and are combined in different immunization regimes with a view to inducing a functional immune response to the four viral serotypes.

13 Claims, 8 Drawing Sheets

Figure 1:
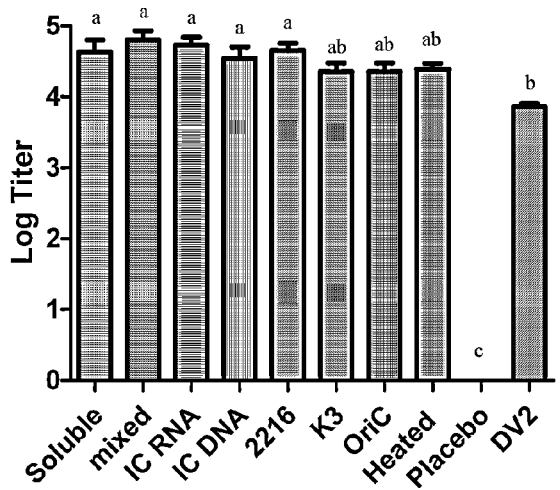

(51) Int. Cl.
 C07K 16/10 (2006.01)
 A61K 39/00 (2006.01)
 C12N 7/00 (2006.01)
(52) U.S. Cl.
 CPC ..... A61K 2039/55561 (2013.01); A61K 2039/70 (2013.01); C07K 14/005 (2013.01); C07K 16/10 (2013.01); C12N 7/00 (2013.01); C12N 2770/00 (2013.01); C12N 2770/24121 (2013.01); C12N 2770/24122 (2013.01); C12N 2770/24134 (2013.01); C12N 2770/24151 (2013.01); C12N 2770/24161 (2013.01)

(56) References Cited

U.S. PATENT DOCUMENTS

| | | | | |
|---|---|---|---|---|
| 7,566,457 | B2* | 7/2009 | Cruz | C07K 14/005 424/186.1 |
| 7,790,173 | B2* | 9/2010 | Lazo Vazquez | A61K 39/12 424/192.1 |
| 7,947,281 | B2* | 5/2011 | Cruz | C07K 14/005 424/186.1 |
| 8,105,606 | B2* | 1/2012 | Cruz | C07K 14/005 424/186.1 |
| 8,722,742 | B2* | 5/2014 | Reyes | A61K 31/16 514/231.2 |
| 2004/0234951 | A1* | 11/2004 | Hermida Cruz | C07K 14/005 435/5 |
| 2007/0071775 | A1* | 3/2007 | Campos Gomez | A61K 39/107 424/261.1 |
| 2007/0141081 | A1* | 6/2007 | Cruz | C07K 14/005 424/204.1 |
| 2009/0274718 | A1* | 11/2009 | Cruz | C07K 14/005 424/190.1 |
| 2009/0312190 | A1* | 12/2009 | Chinea Santiago | A61K 39/12 506/8 |
| 2011/0200628 | A1* | 8/2011 | Cruz | C07K 14/005 424/185.1 |

OTHER PUBLICATIONS

Kuhn et al., "Structure of Dengue Virus: Implications for Flavivirus Organization, Maturation, and Fusion," Cell, vol. 108, 717-725, 2002.
Simmons et al., "Short Report: Antibody Responses of Mice Immunized with a Tetravalent Dengue Recombinant Protein Subunit Vaccine," Am. J. Trop. Med. Hyg., vol. 65(2), pp. 159-161 2001.
Hermida et al., "A dengue-2 Envelope fragment inserted within the structure of the P64k meningococcal protein carrier enables a functional immune response against the virus in mice," Journal of Virological Methods, vol. 115, pp. 41-49, 2004.
Lazo et al., "A recombinant capsid protein from Dengue-2 induces protection in mice against homologous virus," Science Direct Vaccine vol. 25, pp. 1064-1070, 2007.
Gil et al., "Recombinant nucleocapsid-like particles from dengue-2 virus induce protective CD4+ and CD8+ cells against viral encephalitis in mice," International Immunology, vol. 21, No. 10, pp. 1175-1183, 2009.
Lopez et al., "In vitro assembly of nucleocapsid-like particles from purified recombinant capsid protein of dengue-2 virus," Arch. Virol, vol. 154, pp. 695-698, 2009.
Valdes et al., "A novel fusion protein domain III-capsid from dengue-2, in a highly aggregated form, induces a functional immune response and protection in mice," Science Direct Virology, vol. 394, pp. 249-258, 2009.
Clements et al., "Development of a recombinant tetravalent dengue virus vaccine: Immunogenicity and efficacy studies in mice and monkeys," Science Direct Vaccine, doi:10.1016/j.vaccine.2010.01.022., 2010.
Valdes et al., "The Chimeric Protein Domain III-Capsid of Dengue Virus Serotype 2 (DEN-2) Successfully Boosts Neutralizing Antibodies Generated in Monkeys upon Infection with DEN-2," Clinical and Vaccine Immunology, vol. 18, No. 3, pp. 455-459, 2011.
Lazo et al., "A vaccine formulation consisting of nucleocapsid-like particles from Dengue-2 and the fusion protein P64k-domain III from Dengue-1 induces a protective immune response against the homologous serotypes in mice," Acta Tropica, vol. 124, pp. 107-112, 2012.
Gagnon et al., "Bystander Target Cell Lysis and Cytokine Production by Dengue Virus-Specific Human CD4+ Cytotoxic T-Lymphocyte Clones," Journal of Virology, vol. 73, No. 5, pp. 3623-3629, 1999.
Gagnon et al., "Identification of Two Epitopes on the Dengue 4 Virus Capsid Protein Recongnized by a Serotype-Specific and a Panel of Serotype-Cross-Reactive Human CD4+ Cytotoxic T-Lymphocyte Clones," Journal of Virology, vol. 70, No. 1, pp. 141-147, 1996.
Riedl et al., "Priming Th1 Immunity to Viral Core Particles is Facilitated by Trace Amounts of RNA Bound to Its Arginine-Rich Domain," The Journal of Immunology, vol. 168, pp. 4951-4959, 2002.
Crill et al., "Monoclonal Antibodies That Bind to Domain III of Dengue Virus E Glycoprotein Are the Most Efficient Blockers of Virus Adsorption to Vero Cells," Journal of Virology, vol. 75, No. 16, pp. 7769-7773, 2001.
Chen et al., "Demonstration of Binding of Dengue Virus Envelope Protein to Target Cells," Journal of Virology, vol. 70, No. 12, pp. 8765-8772, 1996.
Yauch et al., "A Protective Role for Dengue Virus-Specific CD8+ T Cells," The Journal of Immunology, vol. 182, pp. 4865-4873, 2009.
Bhamarapravati et al., "Live attenuated tetravalent dengue vaccine," Vaccine, vol. 18, pp. 44-47, 2000.
Kanesa-Thasan et al., "Safety and immunogenicity of attenuated dengue virus vaccines (Aventis Pasteur) in human volunteers," Vaccine, vol. 19, pp. 3179-3188, 2001.
Morrison et al., "A Novel Tetravalent Dengue Vaccine is Well Tolerated and Immunogenic against All 4 Serotypes in Flavivirus-Naive Adults," The Journal of Infectious Diseases, vol. 201, pp. 370-377 2010.
Leyssen et al., "Perspectives for the Treatment of Infections with Flaviviridae," Clinical Microbiology Reviews, vol. 13, No. 1, pp. 67-82, 2000.
Hombach, J., "Vaccines against dengue: a review of current candidate vaccines at advanced development stages," Rev Panam Salud Publica/Pan Am J Public Health, vol. 21(4), pp. 254-260, 2007.
Guzman, Maria G., et al., "Domain III of the envelope protein as a dengue vaccine target," Expert Reviews Vaccines, vol. 9(2), pp. 137-147, 2010.
Guzman et al., "Dengue: an update," The Lancet Infectious Diseases, vol. 2, pp. 33-42, 2002.
Verthelyi et al., "Human Peripheral Blood Cells Differentially Recognize and Respond to Two Distinct CpG Motifs," The Journal of Immunology, vol. 166, pp. 2372-2377, 2001.
Krug et al., "Identification of CpG oligonucleotide sequences with high induction of IFN-$\alpha/\beta$ in plasmacytoid dendritic cells," Eur. J. Immunol. vol. 31, pp. 2154-2163, 2001.
Vollmer, J., "CpG Motifs to Modulate Innate and Adaptive Immune Responses," International Reviews of Immunology, vol. 25, pp. 125-134, 2006.
Klinman, D., "Adjuvant Activity of CpG Oligodeoxynucleotides," International Reviews of Immunology, vol. 25, pp. 135-154, 2006.
Mongkolsapaya et al., "Original antigenic sin and apoptosis in the pathogenesis of dengue hemorrhagic fever," Nature Medicine, vol. 9, No. 7, pp. 921-927, 2003.

* cited by examiner

DENGUE VIRUS VACCINE COMPOSITION

This application is the U.S. National Phase of, and Applicant claims priority from, International Patent Application Number PCT/CU2013/000008 filed Dec. 16, 2013, which claims priority from CU 2012-0179 filed Dec. 27, 2012, each of which is incorporated herein by reference.

TECHNIQUE FIELD

The present invention relates to the field of biotechnology and the pharmaceutical industry, particularly with the obtaining of a vaccine formulation against dengue virus (DV) based on recombinant protein antigens and an oligonucleotide with a defined sequence.

BACKGROUND OF THE PREVIOUS TECHNIQUE

Dengue fever is a viral disease transmitted by arthropods most widespread affecting human population. Each year they are reported between 50 and 100 million cases of Dengue, 500 000 of them result in the most severe form of the disease, known as Dengue hemorrhagic fever (Guzman et al., Lancet Infect. Dis. 2002; 2:33-42). The causal agent of this disease is the DV, belonging to the family Flaviviridae, genus *flavivirus*. DV is a viral complex comprising four serotypes. It is an enveloped virus whose lipid membrane contains two of its three structural proteins: the envelope protein and membrane protein. This lipoprotein envelope surrounds the icosahedral nucleocapsid composed by the third of their structural proteins, the capsid protein. (Leyssen et al., Clin. Microbiol. Rev. 2000; 13:67-82).

In the recent decades, the global spread of infections with these viruses has made the development of an effective vaccine, a public health priority. This purpose has been limited by several factors. First of all, infection with one serotype does not induce long-lasting cross protection against the remaining serotypes (Leyssen et al., Clin. Microbiol. Rev. 2000; 13:67-82) and, at the same time, heterotypic secondary infections are the main risk factor for the development of severe forms of the disease (Guzman et al., Lancet Infect. Dis. 2002; 2:33-42; Mongkolsapaya et al., Nat. Med. 2003; 9:921-927). Therefore, an ideal vaccine against DV should induce a long lasting protective immunity against the four viral serotypes (DV1, DV2, DV3 and DV4).

The most advanced vaccine candidates are based on attenuated viral strains through serial passages in cell cultures, or obtained by recombinant way. The viral interference, among the four serotypes in the tetravalent formulations, is the main limitation of this type of candidates making difficult to induce an equivalent functional immune response against the four serotypes; furthermore, they require to be administrated at long intervals between the two or three vaccine doses proposed. (Bhamarapravati et al., Vaccine. 2000; 18:44-47; Kanesa-Thasan et al., Vaccine. 2001; 19:3179-3188; Morrison et al., J. Infect. Dis. 2010; 201:370-377). In addition, due to their nature as live viruses, they cannot be administrated in children less than one year of age.

As an attractive alternative, a series of preclinical studies based on subunit vaccines have been developed. This approach has three key advantages over vaccination with live attenuated virus: 1) they are potentially safe vaccines, 2) the phenomenon of viral interference should not occur due to the non-replicative nature of the immunogen and 3) Short vaccination schemes can be proposed, contrary to the administrations of live attenuated virus which require long intervals between vaccine doses to achieve the booster effect.

One of the most promising subunit vaccine candidates, is developed by the company Hawaii Biotech/Merck (Hombach, Rev. Panam. Salud Publica. 2007; 21:254-260). It is a candidate formed by each viral envelope protein from the four serotypes, expressed in insect cells. Monovalent and tetravalent formulations have been assessed in mice and monkeys with immunogenicity results similar to those obtained with the attenuated viruses (Clements et al., Vaccine. 2010; 28:2705-2715). Nevertheless, the monovalent formulations required the addition of potent adjuvants, not licensed for human use, to induce a proper immune response. In turn, the tetravalent formulation assessed in non-human primates contained, not only a non-licensed adjuvant, but also the protein NS1 from DV2, which has some homology with endothelial human cells and consequently, it could provoke an autoimmunity disorder. Additionally, there are no data available about the induction of cell-mediated immunity upon administration of this vaccine candidate, an important arm of the immunity, which has been recently identified as having a protective role against dengue. (Gil et al., Viral Immunol. 2009; 22:23-30; Yauch et al., J. Immunol. 2009; 182:4865-4873; Yauch et al., J. Immunol. 2010; 185:5405-5416).

Keeping the advantages associated with the subunit vaccines, and, at the same time, looking for safer immunogenic formulations containing alum as base adjuvant, the group of Cuban researchers has developed a working line based on the capsid protein and the domain III of the envelope protein of dengue virus (Guzman et al., Exp. Rev. Vaccines. 2010; 9:137-147).

The capsid protein from DV is essential in the virion assembly and protects the viral genome being its main function. Its molecular weight is 9-12 kDa (112-127 amino acids) and it has a basic structure since the 25% of its amino acids are Arginine and Lysine. The protein is located within the virion structure, without exposed regions (Kuhn et al., Cell. 2002; 108:717-725), making it attractive to be included into a vaccine, due to it may not be target of immune-enhancer antibodies. On the other hand, various human CTL epitopes have been identified on its sequence, providing the induction of an effective cell-mediated immunity against the virus (Gagnon et al., J. Virol. 1996; 70:141-147; Gagnon et al., J. Virol. 1999; 73:3623-3629).

Although there are several studies on the structural characteristics of this capsid protein, it was not until the year 2007 that it was evaluated for the first time in terms of immunogenicity in mice. In this study, the capsid from DV2, was obtained as recombinant protein in *Escherichia coli*. Upon a semi purification process, the resultant preparation was assessed in mice, and partial protection after DV2 challenge was obtained without induction of neutralizing antibodies. (Lazo et al., Vaccine. 2007; 25:1064-1070). Later on, purification and in vitro aggregation process was established at lab scale, and again, the resultant protein was assessed in mice to measure its functionality in terms of protection (Lopez et al., Arch. Virol. 2009; 154:695-698). The analysis of immunogenicity revealed the induction of cell-mediated immunity measured by secretion of gamma interferon (IFN-γ), by the splenocytes of mice receiving the aggregated protein. Such a secretion was dependent on $CD4^+$ and $CD8^+$ cells. In turn, upon challenge with DV2, a significant protection was obtained in animals immunized with the aggregated protein and such a protection was also dependent on $CD4^+$ and $CD8^+$ cells (Gil et al., Int. Immunol.

2009; 21:1175-1183). Based on the aforementioned results, it was proposed to combine, in the same genetic construct, the capsid protein and the DomIII region of the envelope protein, both from DV2. DomIII has been widely described as one receptor-binding region (Chen et al., J. Virol. 1996; 70:8765-8772) and, additionally, it has been reported the induction of neutralizing antibodies and protection in mice immunized with fusion proteins containing this viral region. (Crill et al., J. Virol. 2001; 75:7769-7773; Hermida et al., J. Virol. Methods. 2004; 115:41-49; Simmons et al., Am. J. Trop. Med. Hyg. 2001; 65:159-161). In turn, in non-human primates experiments, it has been demonstrated the induction of a protective immune response only using the Freund's adjuvant (Hermida et al., Vaccine. 2006; 24:3165-3171).

The union viral capsid and the DomIII of the viral envelope protein allows the presence of the two regions potentially protective in a same molecule, capable of simultaneously inducing neutralizing antibodies (DomIII) and cellular immune response (capsid). It was then obtained the genetic construct named DIIIC-2 (DomIII fused to the N-terminus region of the capsid protein, serotype 2), which was expressed in E. coli; and the resulting protein was purified at lab scale, and underwent the process of aggregation with a mixture of oligonucleotides of unknown sequence. Upon inoculation of three doses in mice, antiviral and neutralizing antibodies were detected. In a similar way, significant IFN-γ secretion was detected in splenocytes from animals immunized with the aggregated protein. Consistently with the cell-mediated immunity, a significant protection upon intracranial challenge was obtained, and such a protection was mediated by $CD4^+$ and $CD8^+$ cells induced during the immunization process (Valdes et al., Virology. 2009; 394:249-258). Taken together, the aforementioned results allowed selecting the aggregated form of DIIIC-2 for subsequent studies in non-human primates. The first study in non-human primates was accomplished using animals previously infected with DV2, with the main objective to know the booster capacity of DIIIC2. As expected, after administration of DIII-C2, three months after the virus infection, animals developed high levels of antiviral and neutralizing antibodies against the homologous virus, indicating the presence of functional epitopes within the recombinant protein (Valdes et al., Clin. Vaccine Immunol. 2011; 18:455-459).

As a background of this invention, it was known that addition of oligodeoxinucleotides to form aggregate variants of the protein DIIIC-2 favored the cell-mediated immunity and protection against the homologous virus in mice (Valdes et al., Virology. 2009; 394:249-258). Nevertheless, it was unknown whether the sequence can influence on the quality of the induced immune response.

According to the previous referred elements, the development of a vaccine against DV able to induce a safe and effective immune response against the four serotypes is a non-solved problem. The present invention is precisely directed to this objective.

EXPLANATION OF THE INVENTION

The present invention solves the aforementioned problem, providing a vaccine composition comprising: a) at least one antigen comprising at least the 50% capsid protein sequence from DV and b) the oligodeoxinucleotide identified as SEQ ID NO. 1. In one embodiment of the invention, the vaccine composition is characterized because the antigen comprising at least the 50% capsid protein sequence from DV is a recombinant antigen containing the amino acids from 1 to 99 of such an antigen. In one embodiment of the invention, the vaccine composition comprises a chimeric antigen comprising the amino acids 1 to 99 of the capsid protein and the amino acids 286 to 426 of the DomIII region of the viral envelope protein. In one particular embodiment said recombinant antigens are selected within the group composed by SEQ ID NO. 5 (antigen DIIIC-1), SEQ ID NO. 6 (antigen DIIIC-2), SEQ ID NO. 7 (antigen DIIIC-3) and SEQ ID No. 8 (antigen DIIIC-4).

To demonstrate if the oligonucleotide employed for the protein aggregation influences on the induction of a better immune response, the composition of serotype 2 was selected as a model. The protein DIIIC-2 (chimeric antigen comprising the DomIII of the viral envelope protein and the amino acids 1 to 99 of the capsid protein from DV2) was precipitated in the presence of various oligonucleotides of known sequence, described in the state of the art. It is known that some of these oligonucleotides have adjuvant capacity (Klinman, Int. Rev. Immunol. 2006; 25:1-20; Vollmer, Int. Rev. Immunol. 2006; 25:125-134). A new oligonucleotide was additionally included in the study, formed by the fusion of two of the mentioned oligonucleotides (Krug et al., Eur. J. Immunol. 2001; 31:2154-2163; Verthelyi et al., J. Immunol. 2001; 166:2372-2377). Upon assessment in mice, we demonstrated that the new oligonucleotide (SEQ ID NO. 1) favored the best cell-mediated immunity, measured by IFN-γ secretion; therefore, it was selected to perform the protection assay using the mouse encephalitis model with the homologous virus. As a result, the DIIIC-2 formulation containing the oligonucleotide of SEQ ID NO. 1 and adjuvanted on alum, elicited a potent protective immune response measured by survival percentage and virus titers in brain.

Therefore, in the present invention is demonstrated, for the first time, that the nature of the oligonucleotide is crucial for the induction of a proper cellular immune response, and consequently in the protective capacity of the recombinant protein. Despite trying several oligonucleotides, only one of them, the oligonucleotide whose sequence is identified as SEQ ID NO. 1, turned out to be the best in terms of induction of cellular immune response and protection. Several synthetic oligonucleotides of different sequences were tested, containing or not CpG motifs and having phosphodiester bonds in their structures. This last element differs from oligonucleotides with immunopotentiator activity described in the literature, since links, which are used for the synthesis of these oligonucleotides, are of the type phosphorothioate, in order to protect them from degradation by exonuclease. Additionally, several sizes were tested such as such as 19, 20 and 39 bases. This last 39 bases oligonucleotide contains a number of CpG motifs, and a provision within the sequence, which does not allow including it within the classifications described for oligonucleotides with immnunopotentiator activity in the State of the art. On the other hand, in all cases these molecules were used for aggregation of recombinant antigens, therefore minimum quantities of them were added. This constitutes another element of difference between the employed oligonucleotides as stimulators of the immune system, as large amounts of them are required to promote that function (Riedl et al., J. Immunol. 2002; 168:4951-4959).

As described above, upon immunological assessment in mice we showed that, unexpectedly, the oligonucleotide whose sequence is identified as SEQ ID NO. 1, significantly potentiated the cellular and protective immune response induced by the recombinant protein DIIIC-2, with differences compared to the rest of the employed oligonucleotides.

Then, the concept in negative to dengue non-human primates was proven. Animals received four doses of aggregated DIIIC-2 formulation with the oligonucleotide of SEQ ID NO. 1, and adjuvanted on alum. Additionally, another group of animals was included in the study, receiving a recombinant antigen comprising amino acids 1-99 of the capsid protein from DV2, previously incubated with the oligonucleotide of SEQ ID NO. 1 and forming nucleocapsid-like particles (NLPs-2).

It was determined the response of antiviral and anti-protein antibodies in addition to the functionality of this response, by the neutralization test, using different strains of DV2 and different cell lines. On the other hand, was also evaluated the cell-mediated immunity by the determination IFN-γ secretion, after the in vitro stimulation of peripheral blood mononuclear cells (PBMC) with the infective DV2. Later on, animals were challenged with DV2, and the presence of the virus in the blood was determined. As a result, the protein induced an antibody response with robust neutralizing activity, measured by six different systems (100% seroconversion), as well as a proper cell-mediated immunity, mediated by IFN-γ secretion, before and after challenge with the virus in monkeys. Consistent with the results of immunogenicity, the vaccinated animals were significantly protected against viral challenge, since in two of the three immunized animals no virus was isolated on any day after the challenge, and the third one just showed up one day with viremia values less than 10 plaque forming units per milliliter (pfu/mL).

This study in nonhuman primates, previously negative for dengue, is the first study on the protective ability of a recombinant protein containing the region of the viral capsid DV. This finding allowed to extrapolate these conditions to the other chimeric proteins obtained, corresponding to serotypes 1, 3 and 4.

Next, we designed and obtained the recombinant proteins corresponding to serotypes 1, 3 and 4, which are called DIIIC-1 DIIIC-3 and DIIIC-4, respectively. All molecules were obtained from *E. coli* with appropriate percentages of expression. In turn, these were purified and were recognized by murine polyclonal antibodies specific against the homologous serotype. In addition, it was determined the correct formation of the disulfide bond in each protein, both by mass spectrometry (for DIIIC-1 DIIIC-2, DIIIC-3 and DIIIC-4) and by loss of recognition against murine polyclonal serum upon reduction-carboxymethylation of the cysteines of the DomIII intra-chain disulfide bond (for DIIIC-1 DIIIC-2 and DIIIC-4).

In the studies included in the present invention it was demonstrated that the chimeric proteins DIIIC of these serotypes (1, 3 and 4), which are described for the first time, also induce functional and protective immune response in mice against homologous serotypes. Additionally, it is found that the mixture of the four chimeric proteins, previously formulated with the oligonucleotide of SEQ ID NO. 1 and adjuvanted on alum, induces response to all four serotypes, both cellular and humoral, and protective in mice, with no antigenic competition.

The four chimeric proteins DIIIC-1, DIIIC-2, DIIIC-3 and DIIIC-4 were aggregated when adding the oligonucleotide of SEQ ID NO. 1; they were then adjuvanted on alum for further evaluation in mice. After administration of three doses, it was possible to detect the presence of antiviral antibodies against all four serotypes in 100% of the immunized animals. Similarly, neutralizing activity was detected in the sera of these mice, measured against the four serotypes. Consistent with this result, when performing the intracranial challenge with viral serotypes 1 and 4, significant protection was obtained in both cases and therefore, the proof of concept of functionality of monovalent and tetravalent formulations evaluated in mice was demonstrated.

The tetravalent formulation was also capable of inducing a functional immune response, both humoral and cellular, in monkeys. For the evaluation of the immunogenicity of this formulation a second study in dengue-negative nonhuman primates was conducted. The animals received three doses of the tetravalent formulation through different routes, according to the study group, and one month after the last dose, the humoral and cellular immune responses induced were determined. As a result, it was found that 100% of the monkeys induced antiviral immune response of neutralizing antibodies against all the viral serotypes. Also, the cellular immune response test revealed the induction of a positive response in all animals tested.

This work, as a whole, demonstrates the protective ability of the four aggregated proteins DIIIC with the oligonucleotide of SEQ ID NO. 1 against all four serotypes of DV.

The invention also comprises a vaccine composition characterized by comprising two of the chimeric antigens which are selected from the group consisting of SEQ ID NO. 5, SEQ ID NO. 6, SEQ ID NO. 7 and SEQ ID No. 8. A further object of the invention is a vaccine composition characterized by comprising four chimeric antigens identified as SEQ ID NO. 5, SEQ ID NO. 6, SEQ ID NO. 7 and SEQ ID No. 8.

In another aspect, the invention provides a nucleic acid which is characterized by the sequence identified as SEQ ID NO. 1. As fully shown in the invention, said nucleic acid is useful for increasing the immune response to a vaccine antigen which comprises at least 50% of the sequence of the capsid protein of DV. In one embodiment of the invention, it is demonstrated the use of the nucleic acid identified as SEQ ID NO. 1 to increase the immune response to a recombinant antigen comprising amino acids 1 to 99 of the capsid protein of DV. In a particular embodiment, the use of the nucleic acid identified as SEQ ID NO. 1 to increase the immune response against the chimeric antigens identified as SEQ ID NO. 5, SEQ ID NO. 6, SEQ ID NO. 7 and SEQ ID No. 8 is disclosed.

Additionally, it is object of the present invention a method of inducing immune responses against DV characterized in that it is administered to a subject a vaccine composition comprising a) at least one antigen that comprises at least 50% of the protein sequence from the capsid of DV and b) the oligonucleotide identified as SEQ ID NO. 1. In one aspect, the invention provides a method of inducing immune responses against DV characterized in that such composition comprises a recombinant antigen comprising amino acids 1 to 99 of said protein. In one embodiment of said method, the recombinant antigen is a chimeric antigen having an amino acid sequence that is selected from the group consisting of SEQ ID NO. 5, SEQ ID NO. 6, SEQ ID NO. 7 and SEQ ID No. 8.

In the invention a study was conducted in mice with the aim of reducing the total dose of each DIIIC protein in the immunization schedule. For this, two different bivalent formulations were administered sequentially, and a third boosting dose was given. As a result, no statistically significant differences between groups tested for any of the four virus serotypes were found, which indicates that it is possible, through sequential administrations of bivalent formulations and booster with tetravalent formulation of DIIIC, comprising the oligonucleotide of SEQ ID NO. 1, to obtain the same levels of immunogenicity that administering three doses of the tetravalent formulation DIIIC, with the oligonucleotide of SEQ ID NO. 1. It is therefore also an object of the invention, a method of inducing immune responses against DV in which the vaccine compositions comprising the chimeric antigens identified as SEQ ID NO. 5, SEQ ID NO. 6, SEQ ID NO. 7 and SEQ ID No. 8 are administered sequentially in bivalent compositions. The invention also provides a method wherein additionally, a booster composition comprising the tetravalent composition of the four chimeric antigens identified as SEQ ID NO. 5, SEQ ID NO. 6, SEQ ID NO. 7 and SEQ ID No. 8 is administered.

As shown in the Examples, the compositions comprising at least one antigen that comprises at least 50% of the sequence of the capsid protein of the DV and the oligonucleotide identified as SEQ ID NO. 1 were immunogenic through different routes, so that in the method of the invention the vaccine composition is administered by the routes that are well known by those skilled people in "the state of art", for example the subcutaneous, the intradermal or intramuscular routes.

BRIEF DESCRIPTION OF THE FIGURES

FIG. 1. Antiviral antibody response in immunized animals. In the Y-axis the log Titers anti-DV2 is plotted, in the X-axis the groups of animals receiving different variants of formulations DIIIC-2. Titers were determined using an amplified capture ELISA using the virus as an antigen. Statistical analysis was performed using Kruskal-Wallis and multiple comparisons using the Dunn's test a posteriori. Different letters indicate statistically significant differences between groups. Data are presented as mean±standard deviation.

FIG. 2. Concentrations of IFN-γ measured by ELISA, after in vitro stimulation of splenocytes from mice immunized with different formulations of DIIIC-2 cultured with DV2 or a negative control preparation (mock). On the Y-axis the concentration of IFN-γ (pg/mL) is shown. In the X-axis the groups that received different formulations of DIIIC-2 are represented. Percentages reflected above each set of points represent the percentage of responders. The dashed line indicates the value above which is considered a positive response. Statistical analysis was performed using a single classification ANOVA, and multiple comparisons between groups were performed through the Tukey's test. Different letters indicate statistically significant differences between groups. Data are presented as mean±standard deviation (n=8).

FIG. 3. Protection assays against DV2. A. Survival curves for immunized mice after intracranial challenge with a lethal strain DV2. The Y-axis represents the percentage of survival and the X-axis represents the observation time after the intracranial challenge. B. Viral quantification in VERO cells, measured from infected brain at day 7 post-challenge. The Y-axis represents the number of pfu/mL obtained after plaquing on VERO cells from brain homogenate of infected mouse. The X-axis represents the study groups. For the survival curve, the statistical analysis was performed according to the Log-rank survival test. Different letters indicate statistically significant differences between groups. Data are representative of two independent experiments (n=10). For viral load, statistical analysis was performed using Kruskal-Wallis and multiple comparisons using the Dunn's test a posteriori. Different letters indicate statistical differences between groups. Data are presented as mean±standard deviation (n=5). The dashed line indicates the 100 pfu/mL.

FIG. 4. Kinetics of anti-DIIIC-2 antibodies generated in monkeys and measured by ELISA. The Y-axis represents the log titer and the X-axis represents time in days during the assay. The black arrows indicate the time of each immunization.

FIG. 5. Kinetics of anti-DV antibodies, as measured by a capture ELISA in monkeys immunized with the placebo (A), with the aggregated protein DIIIC-2 (B) or with the NLPs-2 (C). The Y-axis represents the log 1/title, and the X-axis represents time in days during the assay. The black arrows indicate the time of each immunization and the dashed arrow indicates the day of viral challenge.

FIG. 6. Concentrations of IFN-γ measured by ELISA after in vitro stimulation of peripheral blood mononuclear cells from monkeys, receiving the placebo preparation or DIIIC-2 protein. On the Y-axis the concentration of IFN-γ (pg/mL) is represented and in the X-axis the time of the assay is shown. PBMC from the immunized monkeys were cultured with DV2 or a negative control preparation (mock). Data are presented as mean±standard deviation (n=3). The dashed line indicates the value above which is considered a positive response.

FIG. 7. Viral load in the serum of the monkeys immunized with the Placebo formulation (A), the aggregated protein DIIIC-2 (B) or the NLPs-2 (C), measured by direct plaquing on VERO cells. The right axis corresponds to the loads detected in monkeys 2, 5 and 9 (dashed line). The left axis corresponds to the load detected in the remaining animals. On the X-axis the time (in days) after challenge is shown.

FIG. 8. Cloning strategy for obtaining the genetic constructs pDIIIC-1 pDIIIC-2, pDIIIC-3 and pDIIIC-4.

FIG. 9. Recognition levels of chimeric proteins DIIIC under reducing and non-reducing conditions by mouse polyclonal antibodies with high neutralizing titers to the homologous serotype, as determined by ELISA. On the Y-axis the absorbance values are plotted, and the X-axis represents the tested proteins.

FIG. 10. Antiviral antibody response in immunized animals, measured 15 days after the last immunization. The Y-axis represents the log titer anti-DV, and the X-axis represents the groups of animals receiving each formulation. (A) Anti-DV1 antibody response; (B) anti-DV2 antibody response; (C) anti-DV3 antibody response and (D) anti-DV4 antibody response. Titers were determined using an amplified capture ELISA using each virus as antigen. Statistical analysis was performed using Kruskal-Wallis and multiple comparisons using the Dunn's test a posteriori. Different letters indicate statistically significant differences between groups. Data are presented as mean±standard deviation (n=10).

FIG. 11. Concentrations of IFN-γ measured by ELISA, after in vitro stimulation of splenocytes from mice immunized with monovalent and tetravalent formulations DIIIC (including the oligonucleotide of SEQ ID NO. 1) or with the placebo formulation and stimulated with each protein DIIIC. On the Y-axis the concentration of IFN-γ (pg/mL) is shown. On the X-axis the study groups are represented. Data are presented as mean±standard deviation.

FIG. 12. Survival curves of the immunized mice after intracranial challenge with a lethal strain DV1 (A) and DV4 (B). The Y-axis represents the percentage of survival and the X-axis represents the observation time after the intracranial challenge. Statistical analysis was performed according to the log-rank survival test. Different letters indicate statistically significant differences between groups. Data are representative of two independent experiments (n=9).

Figure 13:
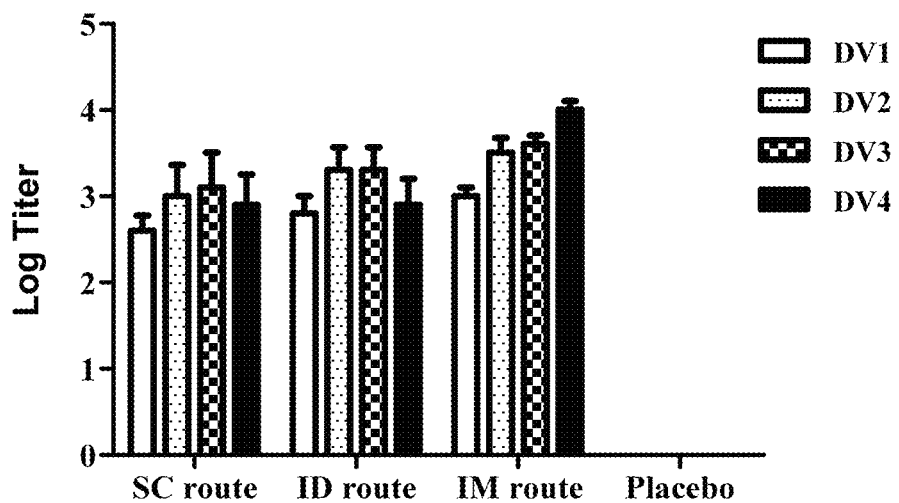

FIG. 13. Antiviral antibody response against all four serotypes of DV as determined by a capture ELISA, after three doses of the tetravalent formulation DIIIC with the oligonucleotide of SEQ ID NO. 1 in non-human primates using the subcutaneous (SC), intradermal (ID) and intramuscular (IM) administration route. The Y-axis represents the Log Title anti-DV and the X-axis the groups of animals.

Figure 2:
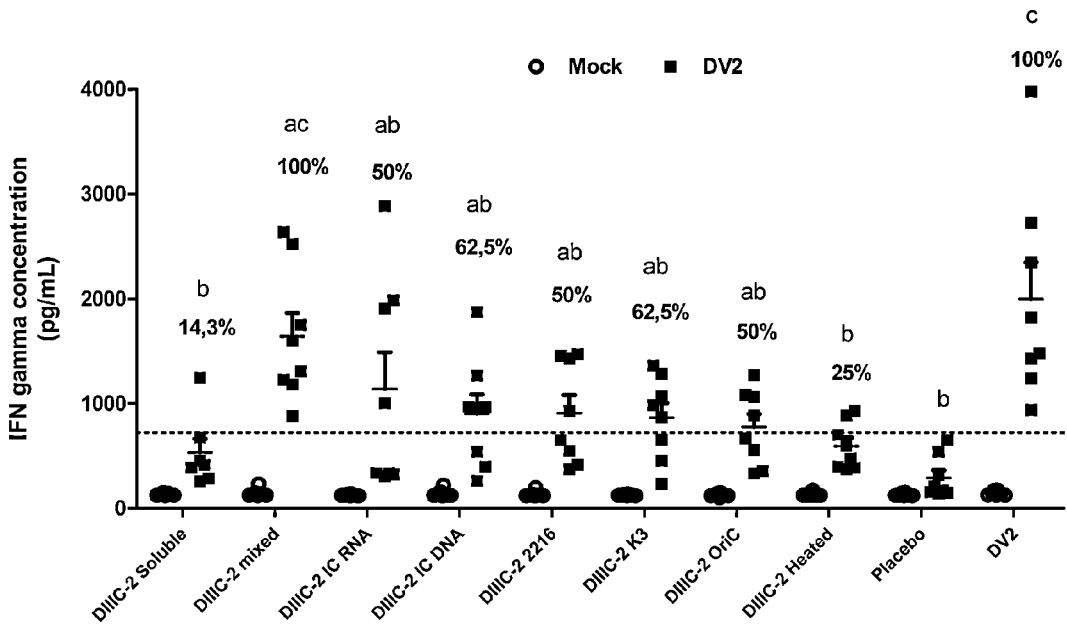
Figure 14:
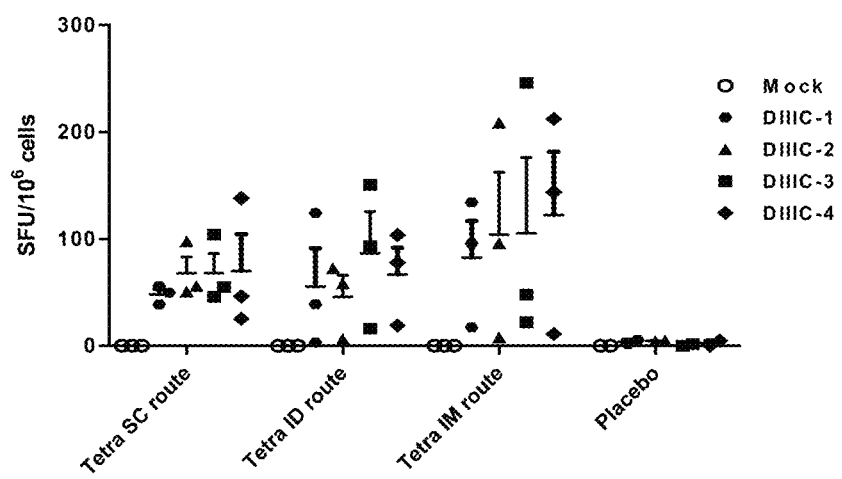
Figure 15:
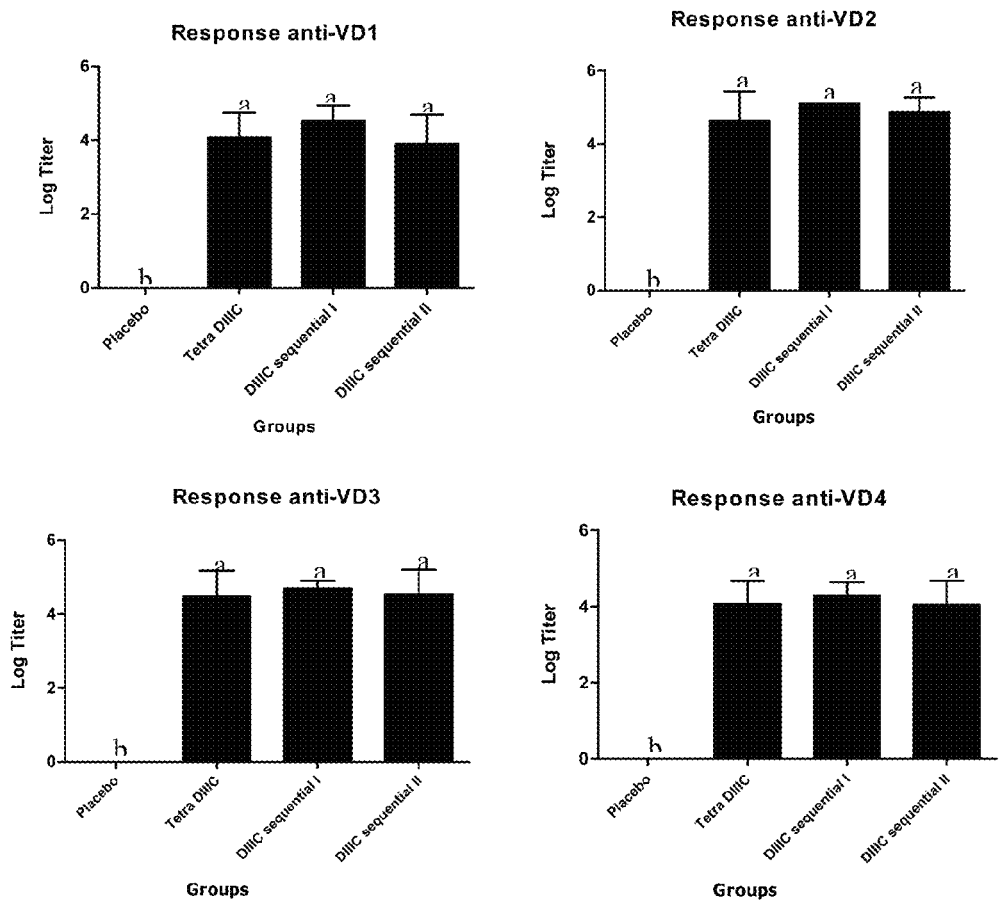
Figure 16:
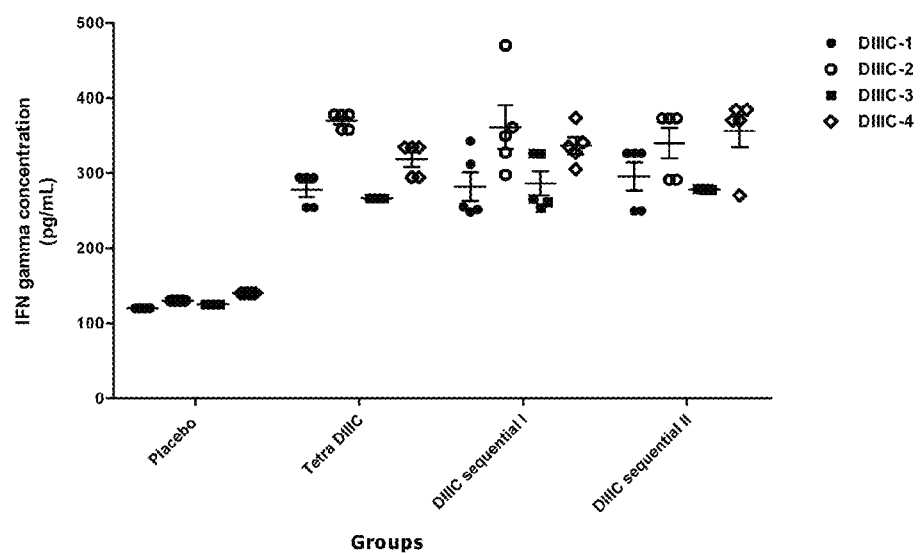

FIG. 14. Frequency of cells producing IFN-γ from the peripheral blood lymphocytes stimulated in vitro with the recombinant proteins DIIIC after three doses of tetravalent formulation DIIIC with oligonucleotide of SEQ ID NO. 1, in non-human primates. In the Y-axis the frequency of cells producing IFN-γ is represented by the number of spots/mL. On the X-axis the animal groups are represented.

FIG. 15. Antiviral antibody response in immunized animals, measured 15 days after the last immunization. The Y-axis represents the log titer anti-DV, and the X-axis the groups of animals receiving each formulation are shown. (A) Anti-DV1 antibody response; (B) anti-DV2 antibody response; (C) anti-DV3 antibody response and (D) anti-DV4 antibody response. Titers were determined using an amplified capture ELISA using each virus as antigen. Statistical analysis was performed using Kruskal-Wallis and multiple comparisons using the Dunn's test a posteriori. Different letters indicate statistical differences between groups. Data are presented as mean±standard deviation (n=10).

FIG. 16. Concentrations of IFN-γ measured by ELISA, after in vitro stimulation of splenocytes from immunized mice and stimulated with each protein DIIIC. On the Y-axis the concentration of IFN-γ (pg/mL) is shown. On the X-axis the study groups are represented. Data are presented as mean±standard deviation (n=5).

DETAILED DESCRIPTION OF EMBODIMENTS/EXAMPLES

Example 1

Evaluation of the Immunogenicity in Mice of the Aggregated Protein DIIIC-2 with Different Oligonucleotides of Defined Sequence Based on the proof of concept in mice with DIIIC-2 protein using a mixture of oligonucleotides of approximately 50 b, of unknown sequence, randomly selected for the aggregation of the protein (Valdes et al, Virology 2009; 394:249-258), various oligonucleotides of defined sequence were tested. Contrary to reports in the literature regarding adjuvant capability of oligonucleotides, those tested in the present study are made only by phosphodiester bonds. Two oligonucleotides of 39 bases were also included, which are not classified within oligonucleotides exerting adjuvant activity, as defined in the literature.

The oligonucleotides tested were:

Oligonucleotide K3 (SEQ ID NO. 2): ATCGACTCTCGAGCGTTCTC, 20 mer (it contains CpG motifs for humans and monkeys. Backbone of phosphodiester bonds)

Oligonucleotide 2216 (SEQ ID NO. 3): GGGGGACGATCGTCGGGGG, 19 mer (it contains CpG motifs for mice and monkeys. Backbone of phosphodiester bonds)

Mixed oligonucleotide (SEQ ID NO. 1): ATCGACTCTCGAGCGTTCTCGGGGGACGATCGTCGGGGG, 39 mer (it contains the sequences of oligonucleotides K3 and 2216, backbone of phosphodiester bonds)

Oligonucleotide OriC (SEQ ID NO. 4): CATACCTCGCTCTGCTAATCCTGTTACCAGTGGCTGCTG 39 mer. (backbone of phosphodiester bonds)

Poly I:C backbone of RNA: ICICICICICICICICICICICICIC 26 mer. (backbone of phosphodiester bonds)

Poly I:C backbone of DNA: ICICICICICICICICICICICICIC 26 mer. (backbone of phosphodiester bonds)

The aggregation reaction was conducted with a mass ratio of protein to the mass of the oligonucleotide to allow the precipitation of 50% of the protein in order to have as constant parameter: equal amounts of soluble and aggregated protein in the formulation.

The aggregate protein DIIIC-2 with different oligonucleotides was evaluated in BALB/c mice. The groups were:

Group 1: Soluble DIIIC-2 (non-aggregate and without oligonucleotide) (20 μg protein)

Group 2: DIIIC-2 with mixed oligonucleotide (SEQ ID NO. 1): (20 μg protein+2 μg oligonucleotide)

Group 3: DIIIC-2 with oligonucleotide poly:IC, ARN (20 μg protein+2 μg oligonucleotide)

Group 4: DIIIC-2 with oligonucleotide poly:IC, ADN (20 μg protein+2 μg oligonucleotide)

Group 5: DIIIC-2 with oligonucleotide 2216 (SEQ ID NO. 3) (20 μg protein+2 μg oligonucleotide)

Group 6: DIIIC-2 with oligonucleotide K3 (SEQ ID NO. 2) (20 μg protein+2 μg oligonucleotide)

Group 7: DIIIC-2 with oligonucleotide OriC (SEQ ID NO. 4) (20 μg protein+2 μg oligonucleotide)

Group 8: Heated DIIIC-2 (control of precipitation without oligonucleotide) (it contains half of the precipitated protein (10 μg) and half soluble (10 μg)

Group 9: Placebo with mixed oligonucleotide (SEQ ID NO. 1) (2 μg)

Group 10: $10^2$ pfu of infective DV2

All variants were formulated on alum as adjuvant base and the animals received three doses every 15 days by intraperitoneal route. After the third dose, the detection of reactive antibodies vs. DV2 was determined by a capture ELISA, whereby the titers by end-point dilution of the sera of these animals were determined. As shown in FIG. 1, high titers of antiviral antibodies for all groups tested were detected, without statistical difference between them ($p>0.05$), indicating that aggregation of the chimeric protein DIIIC-2 does not affect the antiviral antibody response.

With the aim of determining the functionality of the antibodies generated by immunization, the virus neutralization assay in vitro was also performed. Table 1 shows the neutralizing titers against DV2. The neutralizing titer was defined as the highest dilution at which 50% reduction in the number of plates is reached. As can be seen, the animals of all groups were positive by neutralization with 100% seroconversion and Geometric Mean Titles (GMT) greater than 1:70.

TABLE 1

Development of neutralizing antibodies vs. DV2 in the tested groups

| Group | 1 | 2 | 3 | 4 | 5 | 6 | 7 | 8 | 9 | 10 |
|---|---|---|---|---|---|---|---|---|---|---|
| GMT | 153 | 121 | 149 | 73 | 149 | 98 | 107 | 111 | <10 | 69 |

The capacity of aggregated protein DIIIC-2 with different oligonucleotides was also evaluated in this scheme, to generate a cell-mediated immune response. For this, the spleen cells of animals immunized with each variant were extracted and the secretion of IFN-γ in the culture supernatant of splenocytes was measured after stimulation with infectious DV2. FIG. 2 shows the values of cytokine secretion by each group and the percentage of responding animals. Although significant levels of secretion were obtained in all groups, only the group immunized with the aggregated protein with the oligonucleotide of SEQ ID NO. 1 protein showed statistically significant differences with respect to the negative control group. Also, in that group 100% of the animals responded positively. Considering both the percentage of responding animals and the mean value of the concentration of IFN-γ in the cellular immune response test, the formulations of aggregated protein DIIIC-2 with oligonucleotides: mixed (SEQ ID NO. 1), 2216 (SEQ ID NO. 3), K3 (SEQ ID NO. 2), and Ori C (SEQ ID NO. 4) were selected for the protection assay.

For this study, the following groups of 15 mice were formed:
Group 1: DIIIC-2 mixed oligonucleotide (SEQ ID NO. 1) (5 μg protein+0.5 μg oligonucleotide)
Group 2: DIIIC-2 oligonucleotide 2216 (SEQ ID NO. 3) (5 μg protein+0.5 μg oligonucleotide)
Group 3: DIIIC-2 oligonucleotide K3 (SEQ ID NO. 2) (5 μg protein+0.5 μg oligonucleotide)
Group 4: DIIIC-2 oligonucleotide OriC (SEQ ID NO. 4) (5 μg protein+0.5 μg oligonucleotide)
Group 5: Placebo with mixed oligonucleotide (SEQ ID NO. 1) (0.5 μg)
Group 6: $10^2$ pfu of infective DV2

Figure 3:
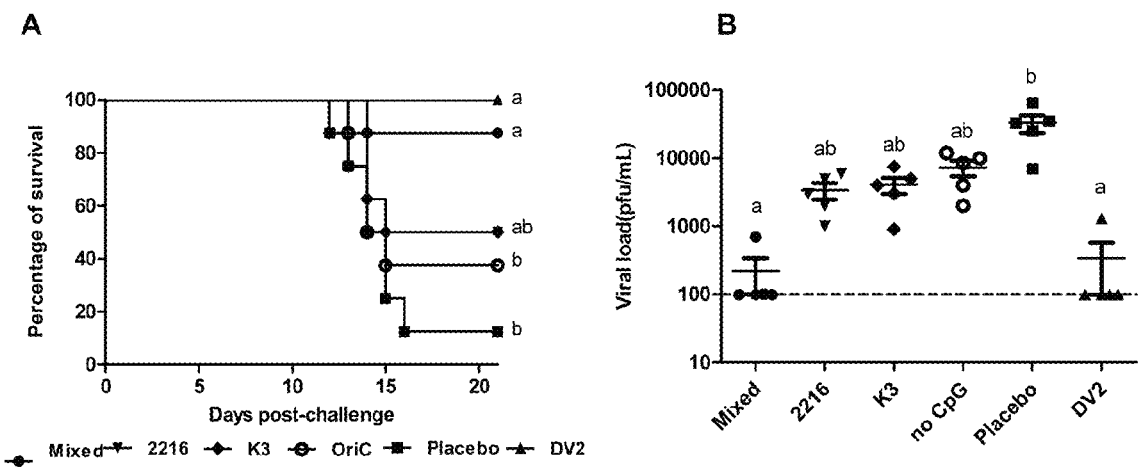

All variants were formulated on alum as adjuvant base and the animals received three doses every 15 days by intraperitoneal route. Two months after the start of the immunization, 10 animals in each group were challenged with 50 median lethal dose ($LD_{50}$) of homologous neuroadapted virus, and were observed for 21 days to measure survival. FIG. 3A describes the survival percentages obtained. As observed, more than 80% of mice receiving the formulation DIIIC-2 with the oligonucleotide of SEQ ID NO. 1 survived the viral challenge without statistically significant differences compared to the positive control group immunized with the DV2 (p>0.05). In turn, only 10% of animals from the negative control group survived the viral challenge, with statistically significant differences from the group immunized with DIIIC-2 and oligonucleotide of SEQ ID NO. 1, and the positive control (p<0.05). Furthermore, animals immunized with formulations containing oligonucleotides 2216, K3 and OriC reached no survival levels with statistically significant differences compared to the placebo group.

The remaining five animals in each group received 500 $LD_{50}$ of the same virus, and 7 days after the viral challenge all animals were sacrificed for removal of the brain, and the viral load was measured in VERO cells. Consistent with the survival observed in FIG. 3A, mice immunized with the formulation DIIIC-2 with the oligonucleotide of SEQ ID NO. 1 had a low viral load in the brain (<$10^2$ pfu/mL), without statistical differences compared to the positive control group (p>0.05), while mice in the group receiving the placebo formulation exhibited a viral load higher than $10^4$ pfu/mL as mean value (FIG. 3B). Animals immunized with formulations containing oligonucleotides 2216, OriC and K3 exhibited intermediate levels of viral load between those achieved with the formulation of DIIIC-2 and the oligonucleotide of SEQ ID NO. 1, and the placebo formulation, with no statistically significant differences between them.

Example 2

Proof of Concept in Nonhuman Primates Immunized with Aggregated Protein DIIIC-2 and Nucleocapsid-Like Particles Obtained from Recombinant Capsid Protein DV2

Based on preclinical studies in mice, we evaluated the aggregated protein DIIIC-2 with the oligonucleotide of SEQ ID NO. 1, and adjuvanted with alum in non-human primates negative to DV. In addition, one group receiving the NLPs-2 (containing the oligonucleotide of SEQ ID NO 1) was evaluated. In turn, the placebo group received a formulation containing the maximum amount of the oligonucleotide of SEQ ID NO. 1, used in the process of aggregation of the recombinant protein adjuvanted on alum. Three animals were included in all groups in the immunization schema.

Figure 4:
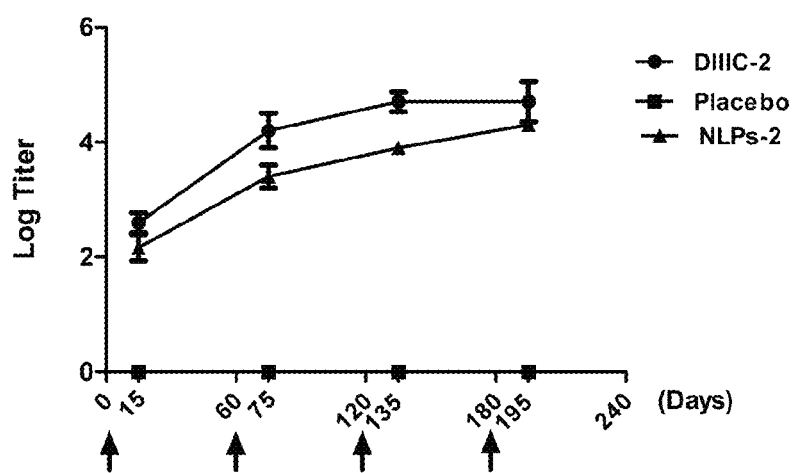
Figure 5:
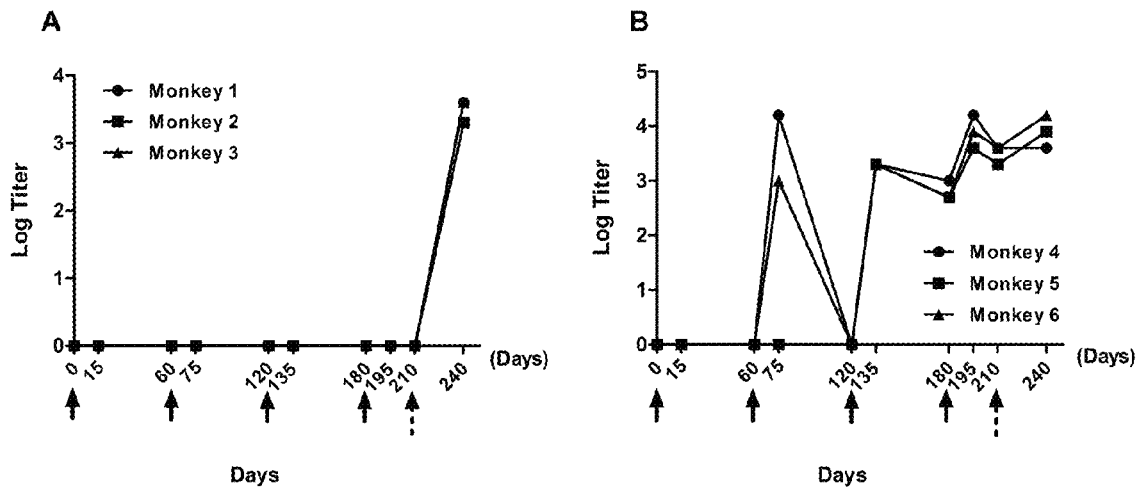

The selected dose for DIIIC-2 was 100 μg of protein and 10 μg of oligonucleotide of SEQ ID NO. 1, while for the NLPs-2 it was 50 μg of protein and 10 μg of oligonucleotide of SEQ ID NO. 1. Monkeys received four doses subcutaneously, every 2 months. Blood was collected at the time of each dose and fifteen days after, to measure the humoral immune response induced. FIG. 4 shows the kinetics of appearance of anti-DIIIC-2 antibodies. As can be seen, in the monkeys that received the formulation DIIIC-2 antibodies began to be detected 15 days after the administration of the first dose. Titers increased following inoculation of the second dose, at values greater than 10,000. After the third dose, titers increased slightly, and after the fourth dose they were kept at the same level (mean mean: 80,000). The response of anti-capsid antibodies in the group immunized with NLPs-2 was similar (FIG. 4). Detection of reactive anti-DV2 antibodies was determined by a capture ELISA, whereby the titers by end-point dilution of the sera of these animals were determined. The results of the kinetic study of the development of antiviral antibodies are shown in FIG. 5. Antiviral antibodies in the monkeys that received the formulation DIIIC-2 with the oligonucleotide of SEQ ID NO. 1, began to be detected 15 days after administration of the second dose (mean value: 6,000), and fell to undetectable levels at the time of the third dose, i.e., 2 months after receiving the second inoculation of the immunogen. Then, after administration of the third dose, the titers increased to similar levels to those obtained 15 days after the second dose, but at this time they remained detectable (mean: 800) when the fourth dose, which corresponded to 2 months after the third dose. Again, upon receiving the fourth inoculation the animals developed antibodies with values slightly higher than those detected at the time of administration, and these were kept until the time of viral challenge with a mean value of 5,000. When the viral dose was given, it was possible to detect a slight increase in antibody titers at 20 and 27 days after challenge, with mean values of 12,000.

The neutralizing antibody response was also measured in this study, since it represents a possible correlate of protection against this virus. Table 2 shows the values obtained for each sample, at indicated times using the Vero cell line and the strain SB8553 DV2.

As observed, neutralizing antibodies can be detected after administration of the second dose of DIIIC-2. Fifteen days after the third inoculation higher titers were detected, which were kept at the time of the fourth administration. After 15 days, the titers increased, showing a clear booster effect. In turn, one month after the last dose, at the time of viral challenge, the high levels of neutralizing antibodies to all animals immunized with DIIIC-2 were detected. For the group receiving the NLPs-2, as expected, no neutralizing response was detected in any of the times evaluated prior to viral challenge (neutralizing titer less than 10, data not shown.) The placebo group behaved similarly with neutralizing titers less than 10 (data not shown).

TABLE 2

Development of neutralizing antibodies vs. DV2 during the immunization scheme in monkeys with DIIIC-2 aggregated protein and the PSNs-2.

|  | Dose 2 | | Dose 3 | | Dose 4 | | Challenge |
| --- | --- | --- | --- | --- | --- | --- | --- |
|  | Month 2 | 15 days | Month 4 | 15 days | Month 6 | 15 days | Month 7 |
| DIIIC-2 | <10 | 150.4 | <10 | 620.5 | 207.1 | 888.1 | 1219.8 |
|  | <10 | <10 | <10 | 23.6 | 26.2 | 79.8 | 57.7 |
|  | <10 | 13 | <10 | 146.2 | 146.5 | 297.7 | 670.3 |
| GMT | <10 | 26.9 | <10 | 128.9 | 92.6 | 276.3 | 361.3 |
| Seroconversion | 0% | 66.7% | 0% | 100% | 100% | 100% | 100% |

One month after the last dose, for the group of DIIIC-2, neutralizing antibodies were also determined, using three viral strains and three different cell lines. In all cases we detected 100% seroconversion, indicating induction of a strong neutralizing response (Table 3).

TABLE 3

Neutralizing antibody titers induced by the aggregated protein DIIIC-2 with the oligonucleotide of SEQ ID NO. 1, at the time of challenge, using three different cell lines and viral strains

|  | Cell line | | | | |
| --- | --- | --- | --- | --- | --- |
|  | BHK-21 | | Vero | | LLC-MK2 |
| Strain DV-2 | A15 | SB8553 | WHO | SB8553 | SB8553 |
| DIIIC-2 | 110 | 415.2 | 3861.4 | 1219.8 | 1143.8 |
|  | 55 | 14.9 | 169.6 | 57.7 | 62.1 |
|  | 150 | 156.2 | 669.7 | 670.3 | 216.1 |
| GMT | 96.8 | 98.9 | 759.8 | 361.3 | 248.5 |
| Seroconversion | 100% | 100% | 100% | 100% | 100% |

Neutralizing titers of each independent animal are shown, as well as GMT and the percentage of seroconversion achieved with the experimental system used.

Figure 6:
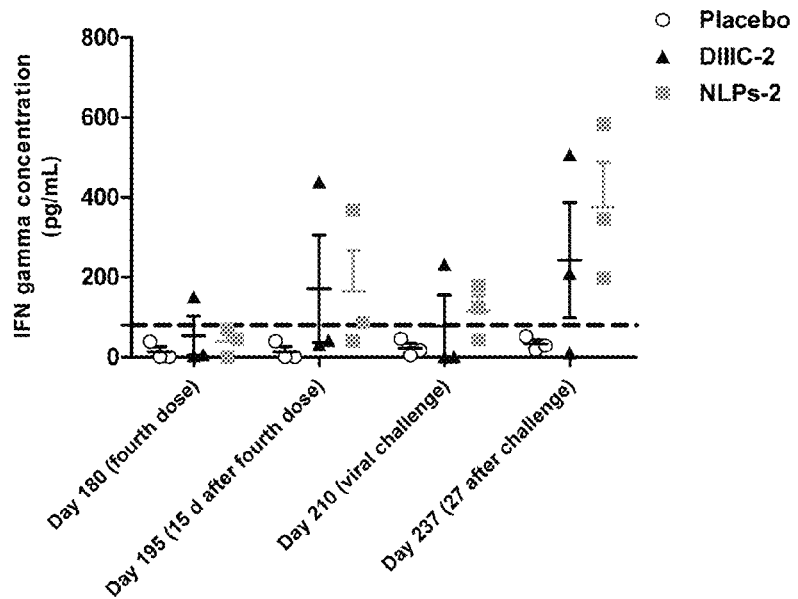

The cellular immune response was another of the parameters measured in this study. Peripheral blood lymphocytes, isolated in four points: day of the fourth dose, 15 days after the fourth dose, day of viral challenge, and 27 days after viral challenge, were stimulated with infective DV2, and the secretion of IFN- was measured γ in the culture supernatant. FIG. 6 shows the values obtained at each tested point. Of the three animals immunized with DIIIC-2 and the oligonucleotide of SEQ ID NO. 1, one (monkey 6) induced secretion of IFN-γ in the three points discussed, before viral challenge. In turn, after the infection, on day 27, another monkey of this group was also positive, indicating a measurement of an anamnestic cellular response.

Moreover, of the three receiving the NLPs-2, two were positive for IFN-γ on day of viral challenge. In turn, after the infection, on day 27, the three monkeys in this group were positive, indicating in this case also the measurement of an anamnestic cellular response. Importantly, none of the animals receiving the placebo formulation had secretion of antiviral cytokines even after the viral challenge.

Figure 7:
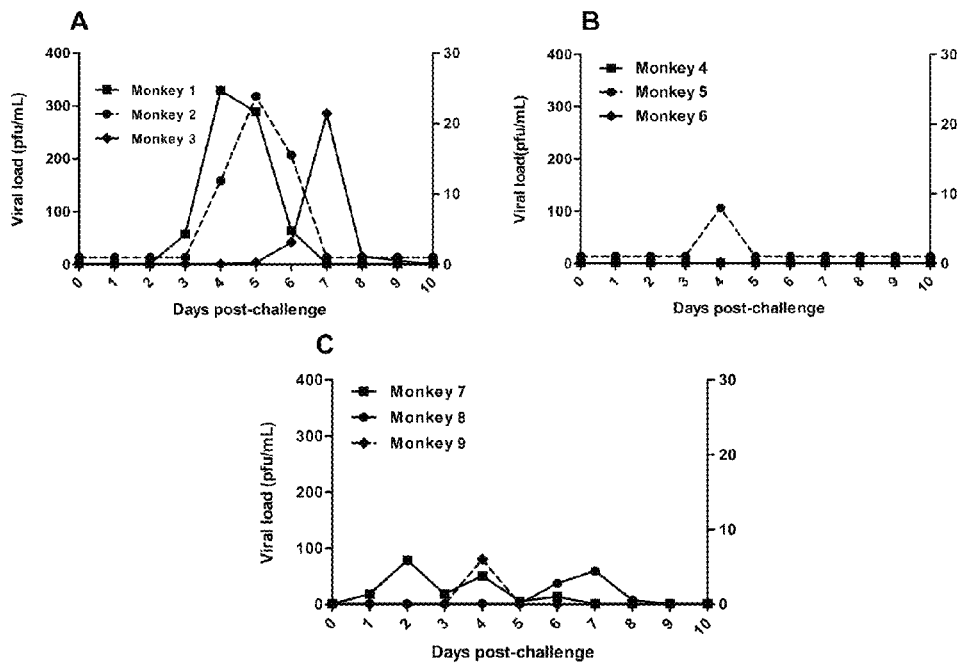
Figure 8:
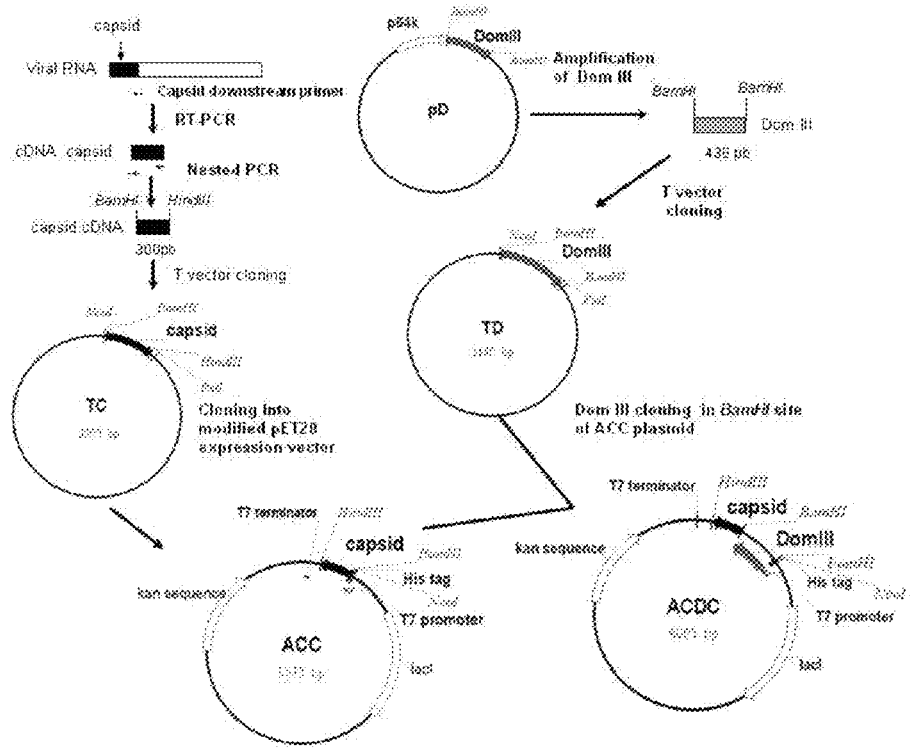
Figure 9:
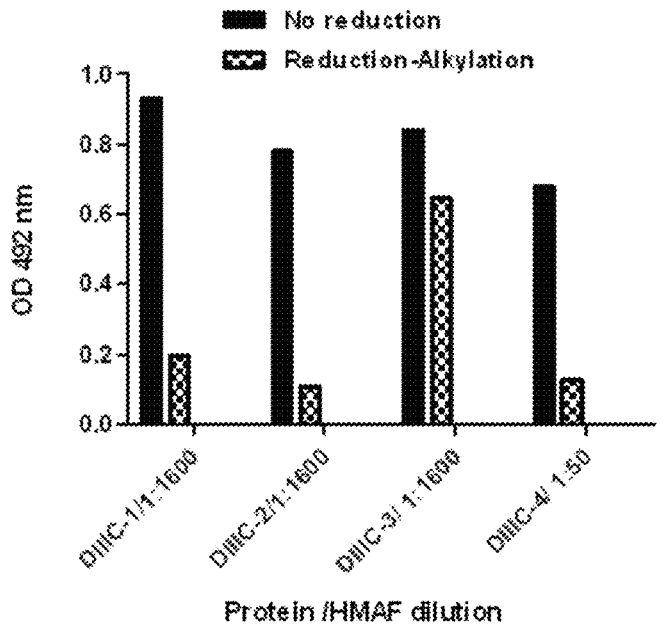

To measure protection against DV2, all experimental animals were challenged with an infective dose of the virus, one month after the last dose. The presence of virus in blood was determined by direct measurement in the VERO cell line. FIG. 7 shows the results obtained; the animals that received the placebo formulation developed viremia for 3.6 days mean value, and with mean viral load of $10^2$ pfu/mL. Conversely, two of the monkeys receiving the DIIIC-2 protein formulation with the oligonucleotide of SEQ ID NO. 1, did not develop viremia and therefore classified as fully protected.

In one animal (monkey 5), the virus was detected on day 5, and with a very low value of viral load (<10 pfu), which also indicates a significant level of protection.

In the case of the group receiving the NLPs-2, the presence of virus was detected in all monkeys, but the viral load was smaller compared to that detected in the control group. In fact, the monkey 9 exhibited a very low viral load (<10 pfu), also indicating a significant level of protection.

In general, we can say that aggregated proteins based on the viral capsid with the oligonucleotide of SEQ ID NO. 1, induce protective response in monkeys.

Example 3

Obtaining and Characterization of Proteins: DIIIC-1 DIIIC-3 and DIIIC-4

The gene fragment BamHI/HindIII containing the DomIII from the envelope protein of DV serotype 1, 3 and 4 (amino acids 286-426) was cloned into the multiple cloning site of the plasmid pET28, fused to the capsid protein of the same virus. This expression vector was previously modified, eliminating the gene sequence between the NcoI and BamHI site, except for the Histidine tag, in order to remove the translation of amino acids not related to the cloned protein. The genetic construct of the plasmids are shown in FIG. 8.

In all cases, the proteins are fused to a Histidine tag at its N-terminus, and are expressed under the regulation of the T7 lac promoter. This allowed, once expressed, developing a process of purification of said proteins by combining ion-exchange chromatography and affinity chromatography with metal chelates. The same methodology was used for purification of the protein DIIIC-2 previously obtained. Once the four recombinant proteins were purified, we proceeded to characterize them. First, the reactivity of each protein was analyzed versus polyclonal sera from mice immunized with each virus preparation, specifically hyperimmune ascitic fluids anti-DV of each serotype (HMAF). As shown in FIG. 9, reactivity was obtained by ELISA of each protein versus HMAF from the homologous viral serotype, indicating a correct presentation of the region DomIII in the context of the capsid, since most of the antibodies generated against viral envelope protein are conformational. Moreover, the state of the disulfide bond (S—S) in the region of DomIII was studied, which must be present in each chimeric molecule. First, it was verified by mass spectrometry each protein, and the correct formation of the bond was verified. Then, based on the fact that the S—S bond is directly involved in the reactivity of DomIII versus polyclonal sera anti-DV, the reactivity of each recombinant protein against the HMAF from the homologous serotype was re-analyzed in reducing and non-reducing conditions. As shown in FIG. 9, for DIIIC-1, 2 and 4 proteins, there was a decreased reactivity against homologous HMAF when proteins are irreversibly reduced by alkylation. For DIIIC-3 a decrease is also observed, although less pronounced than in the rest of the proteins. These results confirm the correct formation of S—S bond and its possible role in the reactivity of DomIII against polyclonal anti-DV antibodies.

Example 4

Immunological Evaluation of Monovalent and Tetravalent Formulations DIIIC in Mice Each chimeric protein previously aggregated with the oligonucleotide of SEQ ID NO. 1 and the tetravalent mixture of four already aggregated molecules were evaluated in BALB/c mice. All preparations were formulated on alum as adjuvant base, and administered in animals in three doses every 15 days intraperitoneally. As positive controls, four groups immunized with each viral serotype were included. As a negative control, one group received a placebo with the same amount of oligonucleotides contained in the tetravalent formulation, and adjuvanted on alum. The amounts of protein for the tetravalent formulation were 20 µg each and 8 µg of total oligonucleotide of SEQ ID NO. 1. Monovalent formulations contained 20 µg of protein and 2 µg of oligonucleotide of SEQ ID NO. 1.

Figure 10:
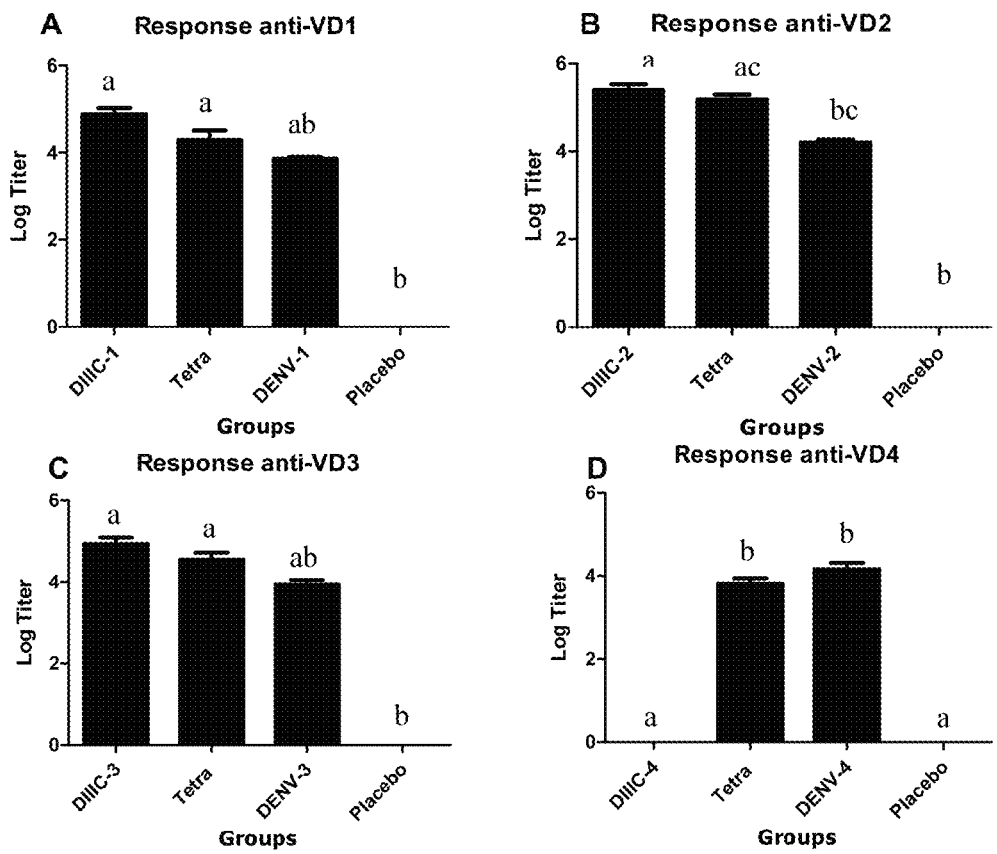

After the third dose, the detection of antibodies reactive with each virus was determined by a capture ELISA (FIG. 10), through which the titers were determined by end-point dilution of the sera of these animals. Animals receiving monovalent formulations had high titers of anti-viral antibodies versus serotypes 1, 2 and 3, whereas animals immunized with DIIIC-4, had no titers against the homologous serotype (DV4). However, animals receiving the tetravalent formulation Tetra-DIIIC developed antibodies against DV4, but with lower titers compared to the other serotypes. This result indicates that the mixture of the four proteins favors the induction of antibodies to DV4, possibly through some level of cross reactivity with the other serotypes.

With the aim of determining the functionality of the antibodies generated by immunization with the tetravalent formulation Tetra-DIIIC, the virus neutralization assay in vitro (Table 4) against the serotype 1, 2, 3 and 4 was carried out. The assay was performed following the guidelines of the World Health Organization (WHO), and using reference strains. Mice immunized with DIIIC-1, 2 and 3 proteins exhibited high titers of neutralizing antibodies against homologous virus, comparable to those elicited by the replicative virus in mice of the control groups. Animals immunized with the DIIIC-4 protein did not show the response, where consistent with the results of the antiviral response, no neutralizing antibodies were detected against DV4. However, the tetravalent formulation, in addition to induce neutralizing antibodies against the serotypes 1, 2 and 3, it also induced functional antibodies against DV4.

TABLE 4

Neutralizing antibody titers in mice immunized with monovalent and tetravalent formulations of the chimeric proteins DIIIC.

| Groups | DV to neutralize | | | |
|---|---|---|---|---|
| | DV1 | DV2 | DV3 | DV4 |
| DIIIC-1 | >500 | — | — | — |
| DIIIC-2 | — | >500 | — | — |
| DIIIC-3 | — | — | >500 | — |
| DIIIC-4 | — | — | — | <10 |
| Tetra DIIIC | 347.1 | >1000 | >1000 | 166.34 |
| Control DV1 | 188.6 | — | — | — |
| Control DV2 | — | >500 | — | — |
| Control DV3 | — | — | >500 | — |
| Control DV4 | — | — | — | >250 |

In all cases a mixture of sera from the mice were analyzed.
—: Not determined.

Figure 11:
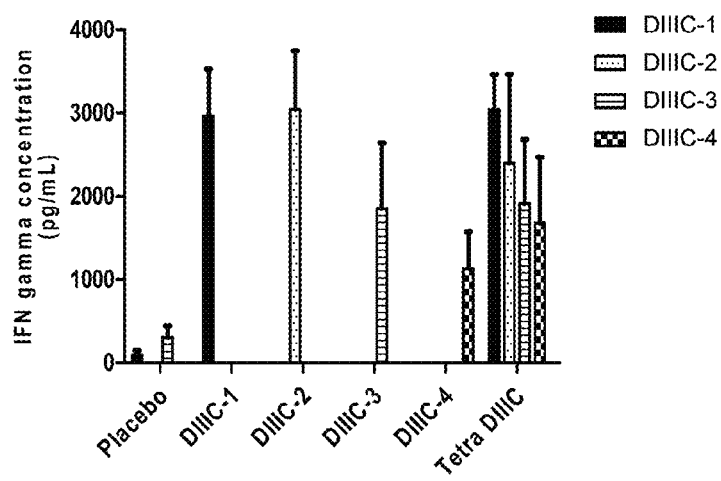

The cellular immune response was another of the parameters measured in this study. For this, the spleen cells of animals immunized with the tetravalent formulation Tetra-DIIIC 30 days after the last dose were extracted and secretion of IFN-γ in the culture supernatant of splenocytes was measured after stimulation with the four recombinant proteins. As negative control, the splenocytes of mice inoculated with the placebo formulation were used. The results obtained are shown in FIG. 11. As observed, high levels of IFN-γ were detected after stimulation with the four recombinant proteins, indicating equivalence in the cellular response obtained to each serotype.

Figure 12:
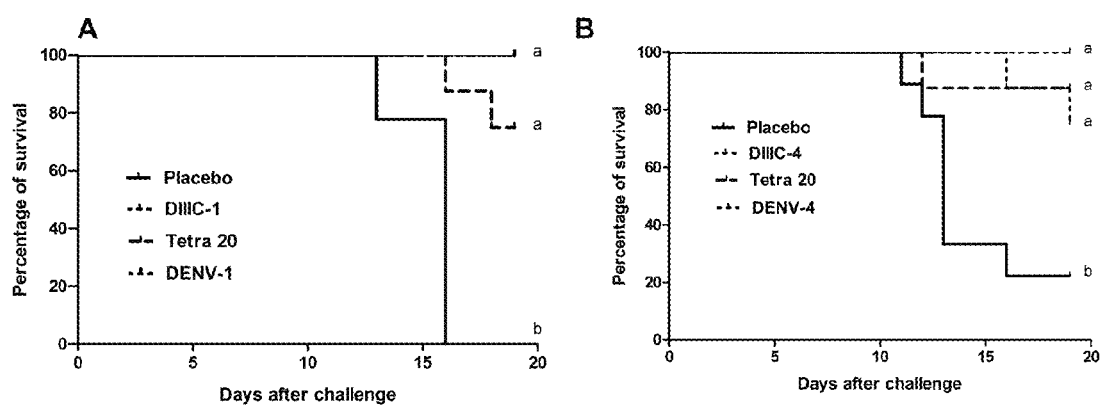

Finally, the protection assay was performed on the model of viral encephalitis in mice. For this experiment, animals immunized with a tetravalent formulation Tetra-DIIIC, monovalent formulations DIIIC-1 and DIIIC-4, the positive control animals (immunized with DV1 and DV4, respectively) and those immunized with the placebo formulation were selected. In turn, the challenge viruses used were DV1 and DV4, capable of causing the death of animals. As shown in FIG. 12, high levels of protection was obtained against serotypes 1 and 4, both with monovalent and tetravalent formulations, in all cases with no statistical differences compared to the viral control group (p>0.05). These results show the protective ability of the formulations tested against serotypes 1 and 4, based on the aggregated proteins DIIIC with the oligonucleotide of SEQ ID NO. 1.

Example 5

Immunological Evaluation in Non-Human Primates of the Tetravalent Formulation Tetra-DIIIC The tetravalent formulation Tetra DIIIC evaluated in mice was similarly assessed in non-human primates. Three study groups of three animals each were formed to receive the tetravalent formulation through three different routes of antigen administration: Group 1: subcutaneous, Group 2: Intradermal and Group 3: intramuscular. Groups 1 and 3 were given 50 µg of each chimeric protein, previously aggregated with 5 µg of oligonucleotide of SEQ ID NO. 1; all mixed and adjuvanted on alum. Group 2 received 10 times less immunogen by intradermal route than the other two routes; it was 5 µg of each protein and 2 µg of total oligonucleotide of SEQ ID NO. 1, all mixed and adjuvanted on alum. The placebo group received the same amount of oligonucleotide of SEQ ID NO. 1 than the groups 1 and 3, adjuvanted on alum and given intramuscularly. Blood was collected at the time of each dose, and one month after them to measure the humoral and cellular immune response induced.

Detection of reactive antibodies to each viral serotype was determined by capture ELISA, whereby the titers by end-point dilution of the sera of these animals were determined. FIG. 13 shows the antiviral antibody response generated in monkeys after three doses of the Tetra-DIIIC formulation including the oligonucleotide of SEQ ID NO. 1. As observed, regardless of the route of antigen administration, monkeys elicited an antibody response capable of recognizing the four viral serotypes in the capture ELISA system. In addition, this response showed a pattern of homogeneity for the four DV; being this an important step toward the development of a vaccine against this human pathogen, which requires a balanced immune response.

The measurement of neutralizing antibodies was performed using the technique of plate reduction neutralization test (PRNT) in VERO cells, and using the viral strains Jamaica DV1, SB8553 DV2, Nicaragua DV3 and Dominica DV4. The values obtained after the third immunization are shown in Table 5.

TABLE 5

Titers of neutralizing antibodies in non-human primates immunized with the tetravalent formulation including Tetra DIIIC with the oligonucleotide of SEQ ID NO. 1.

| Route | DV to neutralize | | | |
|---|---|---|---|---|
| | DV1 | DV2 | DV3 | DV4 |
| Subcutaneous | 77.4 | 215.9 | 146.5 | 46.7 |
| | 253.7 | 186.9 | 138.3 | 102 |
| | 88.5 | 192.9 | 668.1 | 86.1 |
| GMT | 120.2 | 198.2 | 238.3 | 74.3 |
| Intradermal | 57.1 | 153.1 | 617.8 | 35.6 |
| | 44.6 | 184.3 | 165.2 | 42.5 |
| | 49.3 | 88.6 | 200 | 494.2 |
| GMT | 50.1 | 135.7 | 273.3 | 90.8 |
| Intramuscular | 247.2 | 472.7 | 254.3 | 113.1 |
| | 47.7 | 111.4 | 390.3 | 121.6 |
| | 231.6 | 215.9 | 577.5 | 798.5 |
| GMT | 139.8 | 224.9 | 385.6 | 222.3 |

All animals immunized with the formulation Tetra DIIIC generated an antibody response capable of neutralizing viral infection in vitro, regardless of the route of antigen administration. Generating a neutralizing antibody response with 100% of animals responding to all four serotypes is currently a premise on the development of a vaccine against dengue. In the placebo group, the neutralizing titers were lower than 20 in all immunized animals.

The cellular immune response was one of the measured parameters. The PBMCs were stimulated with each of the recombinant proteins DIIIC, and the frequency of cells producing IFN-γ was measured by ELISPOT assay. FIG. 14 shows the values obtained. Following the administration of three doses of tetravalent formulation Tetra-DIIIC, animals generated cells capable of secreting the antiviral cytokine, to stimulation with the recombinant proteins, the response being relatively greater in animals immunized intramuscularly. In all groups evaluated there was a 100% of animals responding to the four proteins tested.

Example 6

Immunological Evaluation in Mice of the Combined Administration of the Bivalent and Tetravalent Formulations of Proteins DIIIC and Oligonucleotide of SEQ ID NO. 1, in Prime-Boost Regime With the purpose of only giving two doses of each protein formulation DIIIC in the same immunization scheme, the following experimental design was carried out:

Sequential Group I dose 1: Bivalent formulation DIIIC-1/DIIIC-2 dose 2: Bivalent formulation DIIIC-3/DIIIC-4 dose 3: Tetravalent formulation Tetra DIIIC

Sequential Group II dose 1: Bivalent formulation DIIIC-1/DIIIC-3 dose 2: Bivalent formulation DIIIC-2/DIIIC-4 dose 3: Bivalent formulation Tetra DIIIC

Group Tetra DIIIC: All doses of tetravalent formulation Tetra DIIIC

Chimeric proteins DIIIC, previously aggregated with the oligonucleotide of SEQ ID NO. 1, were mixed to form both bivalent and tetravalent formulations. The immunogen comprised 20 μg of each protein and 4 μg of oligonucleotide of SEQ ID NO. 1, per bivalent formulation. The amounts of protein for the tetravalent formulation were 20 μg each and 8 μg of total oligonucleotide of SEQ ID NO. 1. All variants were formulated on alum as adjuvant, and were administered every 15 days intraperitoneally. The group that received only the tetravalent formulation Tetra-DIIIC was used as positive control and the placebo group as a negative control.

After the third dose, the detection of antibodies reactive with each virus was determined by a capture ELISA (FIG. 15), through which the titers by end-point dilution of the sera of these animals were determined. As a result, we found that there were no statistically significant differences between the tested groups for any of the four viral serotypes, indicating that is possible, through sequential administrations of bivalent formulations and booster with the tetravalent Tetra-DIIIC, to obtain the same levels of immunogenicity that administering three doses with the tetravalent formulation.

Additionally, the cellular immune response was also measured. Spleen cells from animals immunized from each group of the study were extracted 30 days after the last dose, and the secretion of IFN-γ in the culture supernatant of splenocytes was measured after stimulation with the four recombinant proteins. As negative control, the splenocytes of mice inoculated with the placebo formulation were used. The results obtained are shown in FIG. 16. As can be seen, high levels of IFN-γ were detected after stimulation with the four recombinant proteins in all groups (except for the placebo), indicating equivalence in the cellular response obtained, regardless of the immunization regime used and bivalent formulations administered in the first two doses.

INCORPORATION OF SEQUENCE LISTING

Incorporated herein by reference in its entirety is the Sequence Listing for the application. The Sequence Listing is disclosed on a computer-readable ASCII text file titled, “sequence_listing.txt”, created on Jun. 24, 2015. The sequence_listing.txt file is 10.0 kb in size.

The invention claimed is:

1. An immunogenic composition, wherein said composition comprises: a) at least one protein antigen, wherein said antigen comprises at least 50% of the sequence of the capsid protein of a dengue virus (DV) and b) the oligonucleotide of SEQ ID NO: 1.

2. The composition of claim 1, wherein said protein antigen is a recombinant antigen comprising amino acids 1 to 99 from the starting methionine of said full-length protein.

3. The composition of claim 2, wherein the recombinant antigen is a chimeric antigen selected from the group consisting of SEQ ID NO: 5 (antigen DIIIC-1), SEQ ID NO: 6 (antigen DIIIC-2), SEQ ID NO: 7 (antigen DIIIC-3), and SEQ ID NO: 8 (antigen DIIIC-4).

4. The composition of claim 1, wherein the at least one protein antigen of part a) comprises two chimeric antigens selected from the group consisting of SEQ ID NO: 5, SEQ ID NO: 6, SEQ ID NO: 7 and SEQ ID NO: 8.

5. The composition of claim 1, wherein the at least one protein antigen of part a) comprises four chimeric antigens identified as SEQ ID NO: 5, SEQ ID NO: 6, SEQ ID NO: 7 and SEQ ID NO: 8.

6. An isolated nucleic acid comprising SEQ ID NO: 1.

7. A method of inducing an immune response against DV, wherein the immunogenic composition of claim 1 is administered to a subject.

8. The method of claim 7, wherein said protein antigen is a recombinant antigen comprising amino acids 1 to 99 from the starting methionine of said full-length protein.

9. The method of claim 8, wherein the recombinant antigen is a chimeric antigen selected from the group consisting of SEQ ID NO: 5 (antigen DIIIC-1), SEQ ID NO: 6 (antigen DIIIC-2), SEQ ID NO: 7 (antigen DIIIC-3), and SEQ ID NO: 8 (antigen DIIIC-4).

10. The method of claim 7, wherein the composition is administered subcutaneously, intradermally, or intramuscularly.

11. The method of claim 9, wherein the composition comprises SEQ ID NO:1, SEQ ID NO:5, and SEQ ID NO:6, and is followed by administration of a second booster composition comprising SEQ ID NO:1, SEQ ID NO:7, and SEQ ID NO:8.

12. The method of claim 9, wherein the composition comprises SEQ ID NO:1, SEQ ID NO:5, and SEQ ID NO:7, and is followed by administration of a second booster composition comprising SEQ ID NO:1, SEQ ID NO:6, and SEQ ID NO:8.

13. The method of claim 11 or 12, wherein the method further comprises the administration of a third booster composition comprising SEQ ID NO:1, SEQ ID NO: 5, SEQ ID NO: 6, SEQ ID NO: 7 and SEQ ID NO: 8 following the administration of the second booster composition.

* * * * *

SEQUENCE LISTING

```
<160> NUMBER OF SEQ ID NOS: 8

<210> SEQ ID NO 1
```

-continued

```
<211> LENGTH: 39
<212> TYPE: DNA
<213> ORGANISM: Artificial Sequence
<220> FEATURE:
<223> OTHER INFORMATION: Description of the sequence
      Artificial:Mix Oligonucleotide

<400> SEQUENCE: 1
atcgactctc gagcgttctc gggggacgat cgtcggggg                              39

<210> SEQ ID NO 2
<211> LENGTH: 20
<212> TYPE: DNA
<213> ORGANISM: Artificial Sequence
<220> FEATURE:
<223> OTHER INFORMATION: Description of the sequence
      Artificial:Oligonucleotide K3

<400> SEQUENCE: 2
atcgactctc gagcgttctc                                                   20

<210> SEQ ID NO 3
<211> LENGTH: 19
<212> TYPE: DNA
<213> ORGANISM: Artificial Sequence
<220> FEATURE:
<223> OTHER INFORMATION: Description of the sequence
      Artificial:Oligonucleotide 2216

<400> SEQUENCE: 3
gggggacgat cgtcggggg                                                    19

<210> SEQ ID NO 4
<211> LENGTH: 39
<212> TYPE: DNA
<213> ORGANISM: Escherichia coli

<400> SEQUENCE: 4
catacctcgc tctgctaatc ctgttaccag tggctgctg                              39

<210> SEQ ID NO 5
<211> LENGTH: 252
<212> TYPE: PRT
<213> ORGANISM: Artificial Sequence
<220> FEATURE:
<223> OTHER INFORMATION: Description of the Artificial Sequence:chimeric
      protein DIIIC-1

<400> SEQUENCE: 5

Met Gly His His His His His His Gly Ser Arg Leu Lys Met Asp Lys
 1               5                  10                  15

Leu Thr Leu Lys Gly Met Ser Tyr Val Met Cys Thr Gly Ser Phe Lys
             20                  25                  30

Leu Glu Lys Glu Val Ala Glu Thr Gln His Gly Thr Val Leu Val Gln
         35                  40                  45

Val Lys Tyr Glu Gly Thr Asp Ala Pro Cys Lys Ile Pro Phe Ser Thr
     50                  55                  60

Gln Asp Glu Lys Gly Val Thr Gln Asn Gly Arg Leu Ile Thr Ala Asn
 65                  70                  75                  80

Pro Ile Val Thr Asp Lys Glu Lys Pro Val Asn Ile Glu Thr Glu Pro
                 85                  90                  95

Pro Phe Gly Glu Ser Tyr Ile Val Val Gly Ala Gly Glu Lys Ala Leu
            100                 105                 110
```

```
Lys Leu Ser Trp Phe Lys Lys Gly Ser Ser Ile Gly Lys Met Phe Glu
            115                 120                 125

Ala Thr Ala Arg Gly Ala Arg Arg Met Ala Ile Leu Gly Asp Thr Ala
130                 135                 140

Trp Asp Phe Gly Ser Ile Gly Gly Ser Asn Gln Arg Lys Lys Thr
145                 150                 155                 160

Ala Arg Pro Ser Phe Asn Met Leu Lys Arg Ala Arg Asn Arg Val Ser
                165                 170                 175

Thr Val Ser Gln Leu Ala Lys Arg Phe Ser Lys Gly Leu Leu Ser Gly
            180                 185                 190

Gln Gly Pro Met Lys Leu Val Met Ala Phe Ile Ala Phe Leu Arg Phe
        195                 200                 205

Leu Ala Ile Pro Pro Thr Ala Gly Ile Leu Ala Arg Trp Gly Ser Phe
210                 215                 220

Lys Lys Ser Gly Ala Ile Lys Val Leu Arg Gly Phe Lys Lys Glu Ile
225                 230                 235                 240

Ser Asn Met Leu Asn Ile Met Asn Arg Arg Lys Arg
                245                 250

<210> SEQ ID NO 6
<211> LENGTH: 253
<212> TYPE: PRT
<213> ORGANISM: Artificial Sequence
<220> FEATURE:
<223> OTHER INFORMATION: Description of the Artificial Sequence:chimeric
      protein DIIIC-2

<400> SEQUENCE: 6

Met Gly His His His His His Gly Ser Arg Leu Arg Met Asp Lys
1               5                   10                  15

Leu Gln Leu Lys Gly Met Ser Tyr Ser Met Cys Thr Gly Lys Phe Lys
            20                  25                  30

Ile Val Lys Glu Ile Ala Glu Thr Gln His Gly Thr Ile Val Ile Arg
        35                  40                  45

Val Gln Tyr Glu Gly Asp Gly Ser Pro Cys Lys Ile Pro Phe Glu Ile
    50                  55                  60

Met Asp Leu Glu Lys Arg His Val Leu Gly Arg Leu Ile Thr Val Asn
65                  70                  75                  80

Pro Ile Val Thr Glu Lys Asp Ser Pro Val Asn Ile Glu Ala Glu Pro
                85                  90                  95

Pro Phe Gly Asp Ser Tyr Ile Ile Ile Gly Val Glu Pro Gly Gln Leu
            100                 105                 110

Lys Leu Asn Trp Phe Lys Lys Gly Ser Ser Ile Gly Gln Met Phe Glu
        115                 120                 125

Thr Thr Met Arg Gly Ala Lys Arg Met Ala Ile Leu Gly Asp Thr Ala
130                 135                 140

Trp Asp Phe Gly Ser Leu Gly Gly Ser Asn Asn Gln Arg Lys Lys
145                 150                 155                 160

Ala Arg Ser Thr Pro Phe Asn Met Leu Lys Arg Glu Arg Asn Arg Val
                165                 170                 175

Ser Thr Val Gln Gln Leu Thr Lys Arg Phe Ser Leu Gly Met Leu Gln
            180                 185                 190

Gly Arg Gly Pro Leu Lys Leu Phe Met Ala Leu Val Ala Phe Leu Arg
        195                 200                 205

Phe Leu Thr Ile Pro Pro Thr Ala Gly Ile Leu Lys Arg Trp Gly Thr
210                 215                 220
```

```
Ile Lys Lys Ser Lys Ala Ile Asn Val Leu Arg Gly Phe Arg Lys Glu
225                 230                 235                 240

Ile Gly Arg Met Leu Asn Ile Leu Asn Arg Arg Arg
                245                 250
```

<210> SEQ ID NO 7
<211> LENGTH: 252
<212> TYPE: PRT
<213> ORGANISM: Artificial Sequence
<220> FEATURE:
<223> OTHER INFORMATION: Description of the Artificial sequence:chimeric protein DIIIC-3

<400> SEQUENCE: 7

```
Met Gly His His His His His Gly Ser Arg Leu Lys Met Asp Lys
  1               5                  10                  15

Leu Glu Leu Lys Gly Met Ser Tyr Ala Met Cys Thr Asn Thr Phe Val
                 20                  25                  30

Leu Lys Lys Glu Val Ser Glu Thr Gln His Gly Thr Ile Leu Ile Lys
             35                  40                  45

Val Glu Tyr Lys Gly Glu Asp Val Pro Cys Lys Ile Pro Phe Ser Thr
 50                  55                  60

Glu Asp Gly Gln Gly Lys Ala His Asn Gly Arg Leu Ile Thr Ala Asn
 65                  70                  75                  80

Pro Val Val Thr Lys Lys Glu Pro Val Asn Ile Glu Ala Glu Pro
                 85                  90                  95

Pro Phe Gly Glu Ser Asn Ile Val Ile Gly Ile Gly Asp Asn Ala Leu
                100                 105                 110

Lys Ile Asn Trp Tyr Lys Lys Gly Ser Ser Ile Gly Lys Met Phe Glu
            115                 120                 125

Ala Thr Ala Arg Gly Ala Arg Arg Met Ala Ile Leu Gly Asp Thr Ala
130                 135                 140

Trp Asp Phe Gly Ser Val Gly Gly Ser Asn Gln Arg Lys Lys Thr
145                 150                 155                 160

Gly Lys Pro Ser Ile Asn Met Leu Lys Arg Val Arg Asn Arg Val Ser
                165                 170                 175

Thr Gly Ser Gln Leu Ala Lys Arg Phe Ser Lys Gly Leu Leu Asn Gly
            180                 185                 190

Gln Gly Pro Met Lys Leu Val Met Ala Phe Ile Ala Phe Leu Arg Phe
        195                 200                 205

Leu Ala Ile Pro Pro Thr Ala Gly Val Leu Ala Arg Trp Gly Thr Phe
    210                 215                 220

Lys Lys Ser Gly Ala Ile Lys Val Leu Lys Gly Phe Lys Lys Glu Ile
225                 230                 235                 240

Ser Asn Met Leu Ser Ile Ile Asn Lys Arg Lys Lys
                245                 250
```

<210> SEQ ID NO 8
<211> LENGTH: 252
<212> TYPE: PRT
<213> ORGANISM: Artificial Sequence
<220> FEATURE:
<223> OTHER INFORMATION: Description of the Artificial Sequence:chimeric protein DIIIC-4

<400> SEQUENCE: 8

```
Met Gly His His His His His Gly Ser Lys Val Arg Met Glu Lys
  1               5                  10                  15
```

```
Leu Arg Ile Lys Gly Met Ser Tyr Thr Met Cys Ser Gly Lys Phe Ser
            20              25              30

Ile Asp Lys Glu Met Ala Glu Thr Gln His Gly Thr Thr Val Val Lys
        35              40              45

Val Lys Tyr Glu Gly Ala Gly Ala Pro Cys Lys Val Pro Ile Glu Ile
    50              55              60

Arg Asp Val Asn Lys Glu Lys Val Val Gly Arg Ile Ile Ser Ser Thr
65              70              75              80

Pro Leu Ala Glu Asn Thr Asn Ser Val Thr Asn Ile Glu Leu Glu Pro
            85              90              95

Pro Phe Gly Asp Ser Tyr Ile Val Ile Gly Val Gly Asn Ser Ala Leu
            100             105             110

Thr Leu His Trp Phe Arg Lys Gly Ser Ser Ile Gly Lys Met Phe Glu
        115             120             125

Ser Thr Tyr Arg Gly Ala Lys Arg Met Ala Ile Leu Gly Glu Thr Ala
    130             135             140

Trp Asp Phe Gly Ser Val Gly Gly Gly Ser Asn Gln Arg Lys Lys Val
145             150             155             160

Val Arg Pro Pro Phe Asn Met Leu Lys Arg Glu Arg Asn Arg Val Ser
            165             170             175

Thr Pro Gln Gly Leu Val Lys Arg Phe Ser Thr Gly Leu Phe Ser Gly
            180             185             190

Lys Gly Pro Leu Arg Met Val Leu Ala Phe Ile Thr Phe Leu Arg Val
        195             200             205

Leu Ser Ile Pro Pro Thr Ala Gly Ile Leu Lys Arg Trp Gly Gln Leu
    210             215             220

Lys Lys Asn Lys Ala Ile Lys Ile Leu Ile Gly Phe Arg Lys Glu Ile
225             230             235             240

Gly Arg Met Leu Asn Ile Leu Asn Gly Arg Lys Arg
            245             250
```